United States Patent [19]
Naylor et al.

[11] Patent Number: 5,800,692
[45] Date of Patent: Sep. 1, 1998

[54] PRESEPARATION PROCESSOR FOR USE IN CAPILLARY ELECTROPHORESIS

[75] Inventors: Stephen Naylor; Andrew J. Tomlinson, both of Rochester; Linda M. Benson, Wanamingo; Walter David Braddock, Rochester; Robert P. Oda, Stewartville, all of Minn.

[73] Assignee: Mayo Foundation for Medical Education and Research, Rochester, Minn.

[21] Appl. No.: 423,220

[22] Filed: Apr. 17, 1995

[51] Int. Cl.$^6$ .................... G01N 27/26; G01N 27/447
[52] U.S. Cl. .................... 204/601; 204/451; 204/453; 204/604
[58] Field of Search .................... 204/451, 452, 204/453, 454, 455, 601, 602, 603, 604, 605

[56] References Cited

U.S. PATENT DOCUMENTS

| | | | |
|---|---|---|---|
| 4,705,616 | 11/1987 | Andresen et al. | 204/452 |
| 4,708,782 | 11/1987 | Andresen et al. | 204/600 X |
| 4,842,701 | 6/1989 | Smith et al. | 204/451 |
| 4,865,707 | 9/1989 | Karger et al. | 204/453 |
| 4,885,076 | 12/1989 | Smith et al. | 204/451 |
| 4,895,806 | 1/1990 | Le et al. | 435/288 |
| 4,911,807 | 3/1990 | Burd | 204/453 |
| 4,997,530 | 3/1991 | Ellis et al. | 205/170 |
| 5,006,313 | 4/1991 | Swedberg | 422/70 X |
| 5,084,150 | 1/1992 | Karger et al. | 204/451 |
| 5,089,106 | 2/1992 | Karger et al. | 204/453 |
| 5,126,025 | 6/1992 | Carson et al. | 204/451 |
| 5,131,998 | 7/1992 | Jorgenson et al. | 204/604 X |
| 5,151,164 | 9/1992 | Blanchard et al. | 204/451 |
| 5,169,510 | 12/1992 | Lunte et al. | 204/601 |
| 5,169,511 | 12/1992 | Allington et al. | 204/451 |
| 5,180,475 | 1/1993 | Young et al. | 204/454 |
| 5,202,010 | 4/1993 | Guzman | 204/601 |
| 5,213,669 | 5/1993 | Guttman | 204/452 |

(List continued on next page.)

FOREIGN PATENT DOCUMENTS

| | | | |
|---|---|---|---|
| 297149 A1 | 1/1989 | European Pat. Off. | B01D 57/02 |
| 459241 A1 | 12/1991 | European Pat. Off. | G01N 27/447 |
| 471949 A1 | 2/1992 | European Pat. Off. | G01N 27/447 |
| 500211 A2 | 8/1992 | European Pat. Off. | G01N 27/447 |
| 93/05390 | 3/1993 | WIPO | G01N 27/26 |

OTHER PUBLICATIONS

Liyuan Bao and Purnendu K. Dasgupta, "Membrane Interfaces for Sample Introduction in Capillary Zone Electrophoresis" Analytical Chemistry, vol. 64, No. 9 (May 1, 1992) 991–996.

Fang et al., "On–line Time–of–Flight Mass Spectrometric Analysis of Peptides Separated by Capillary Electrophoresis", Anal. Chem., 66, 3696–3701 (1994).

Swartz et al., "On–line Sample Preconcentration on a Pack-ard–Inlet Capillary for Improving the Sensitivity of Capillary Electrophoretic Analysis of Pharmaceuticals", J. Chromatogr., 632, 209–213 (1993).

Tomlinson et al., "On–Line Preconcentration–Capillary Electrophoresis–Mass Spectrometry (PC–CE–MS)", Journal of High Resolution Chromatography, 17, 729–731 (Oct. 1994).

(List continued on next page.)

Primary Examiner—Kathryn L. Gorgos
Assistant Examiner—John S. Starsiak, Jr.
Attorney, Agent, or Firm—Fish & Richardson P.C.

[57] ABSTRACT

A preseparation processor for use in capillary electrophoresis is described. The preseparation processor contains sample processing material, preferably in the form of a membrane, for use in concentrating or chemically processing a sample, or catalyzing a chemical reaction. It is particularly suited to the concentration of dilute samples or the purification of contaminated samples. The preseparation processor facilitates reliable and reproducible separation of analytes by eliminating inconsistencies caused by a reversal of the electroosmotic flow otherwise induced by the sample processing material.

11 Claims, 8 Drawing Sheets

U.S. PATENT DOCUMENTS

| | | | |
|---|---|---|---|
| 5,228,960 | 7/1993 | Liu et al. | 204/451 |
| 5,240,585 | 8/1993 | Young et al. | 204/601 |
| 5,246,577 | 9/1993 | Fuchs et al. | 204/604 |
| 5,262,031 | 11/1993 | Lux et al. | 204/601 |
| 5,282,941 | 2/1994 | Rose, Jr. | 204/605 |
| 5,290,587 | 3/1994 | Young et al. | 427/122 |
| 5,318,680 | 6/1994 | Fishman et al. | 204/453 |
| 5,340,452 | 8/1994 | Brenner et al. | 204/453 |

OTHER PUBLICATIONS

Linda M. Benson et al., "Time Course Analysis of a Microsomal Incubation of a Therapeutic Drug Using Preconcentration Capillary Electrophoresis (PE–CE)," *Journal of High Resolution Chromatography*, vol. 17, pp. 3–5, No month available (1994).

R–L. Chien et al., "Field amplified sample injection in high–performance capillary electrophoresis", *Journal of Chromatography*, 559, pp. 141–152, No month available (1991).

P. D. G. Dean et al., "Electrophoretic Desorption of Affinity Adsorbents", *Biochemical Society Transaction 569th Meeting, Sussex*, vol. 5, pp. 1111–1113 No date available.

A. J. J. Debets et al., "Switching valve with internal micro precolumn for on–line sample enrichment in capillary zone electrophoresis," *Journal of Chromatography*, 608, pp. 151–158, No month available (1992).

N. A. Guzman et al., "The Use of a Concentration Step to Collect Urinary Components Separated by Capillary Electrophoresis and Further Characterization of Collected Analytes by Mass Spectrometry", *Journal of Liquid Chromatography*, 14(5), pp. 997–1015, No month available (1991).

S. C. Jacobson et al., "Effects of Injection Schemes and Column Geometry on the Performance of Microchip Electrophoresis Devices", *Analytical Chemisry*, vol. 66, No. 7, pp. 1107–1113, No month available (1994).

V. Kasicka et al., "Desorption Isotachophoresis—Quantitative Characterization of Sorption and Desorption Conditions", *Journal of Chromatography*, pp. 75–80, No month available (1985).

V. Kasicka et al., "Determination of Dissociation Constants of Weak Electrolytes by Capillary Isotachophoresis", *Journal of Chromatography*, pp. 33–43, No month available (1985).

V. Kasicka et al., "Isotachophoretic Electrodesorption of Proteins From an Affinity Adsorbent on a Microscale", *Journal of Chromatography*, 273, pp. 117–128.

J. Mark, "Use of a Poroszyme™ Immobilized Trypsin Cartridge for Peptide Mapping" *PerSeptive Biosystems*, No month available (1994).

Master Bond Inc., "Material Safety Data Sheet, A Solvent–Free, Two Component High Performance Epoxy Adhesive/sealant Featuring Resistance to Radiation, Ethylene Oxide & Steam Sterilization, Meeting USP Class VI Requirement", *U.S. Department of Labor, OSHA 174*, No month available (1985).

R. Nelson et al., "Temperature Control in Capillary Electrophoresis," *CRC Handbook of Capillary Electrophoresis*, pp. 549–562, 1994. No date available.

L. Netzer et al., "Adsorbed Monolayers Versus Langmuir–Blodgett Monolayers—Why and How? 1: From Monolayer to Multilayer, By Adsorption", *Thin Solid Films*, 99, pp. 235–241, No month available (1983).

Robert P. Oda et al., "Introduction to Capillary Electrophoresis," *CRC Handbook of Capillary Electrophoresis*, pp. 25–28, No month available (1994).

Z. Prusik et al., "Micropreparative Isotachophoretic Electrodesorption of Monoclonal Antibodies From an Affinity Adsorbent", *Journal of Chromatography*, 320, pp. 81–88, No month available (1985).

W. J. Storkus et al., "Identification of T–Cell Epitopes: Rapid Isolation of Class I–Presented Peptides from Viable Cells by Mild Acid Elution" *Journal of Immunotheraphy*, 14, pp. 94–103 No month available (1993).

A.J. Tomlinson et al., "Effects of Organic Solvent in the CE and On–Line CE–MS Analysis of Drug Metabolite Mixtures," *American Laboratory*, pp. 29–36, (Jun. 1994).

A. Tomlinson et al., "MHC Class I Peptides, Strategy for Isolation and Sequencing of MHC Class I Peptides Using Capillary Electrophoresis and Capillary Electrophoresis–Mass Spectrometry/Mass Spectrometry", *HPCE '94 Conference in San Diego, CA.*, No month available (1994).

A. J. Tomlinson et al., "Analysis of Biologically Derived Biopolymers and Drug Metabilites by Preconcentration–Capillary Electrophoresis–MS", *ASMS '94*, No month available (1994).

A. J. Tomlinson et al., "Modification of Electroosmotic Flow in Preconcentration–Capillary Electrophoresis (PC–CE", *Journal of High Resolution Chromatography* vol. 17, pp. 1–3, No month available (1994).

The United States Pharmacopeia, The National Formulary, *Biological Tests, Biological Reactivity Tests, In Vivo*, vol. 88, pp. 1699–1703, No month available (1995).

3M and Varian International AG, "Empore™ Extraction Disks for Environmental Analysis", Technical Data Brochure No date available.

B.J. Wanders et al., "Isotachophoresis in Capillary Electrophoresis," *CRC Handbook of Capillary Electrophoresis*, pp. 111–127, No month available (1994).

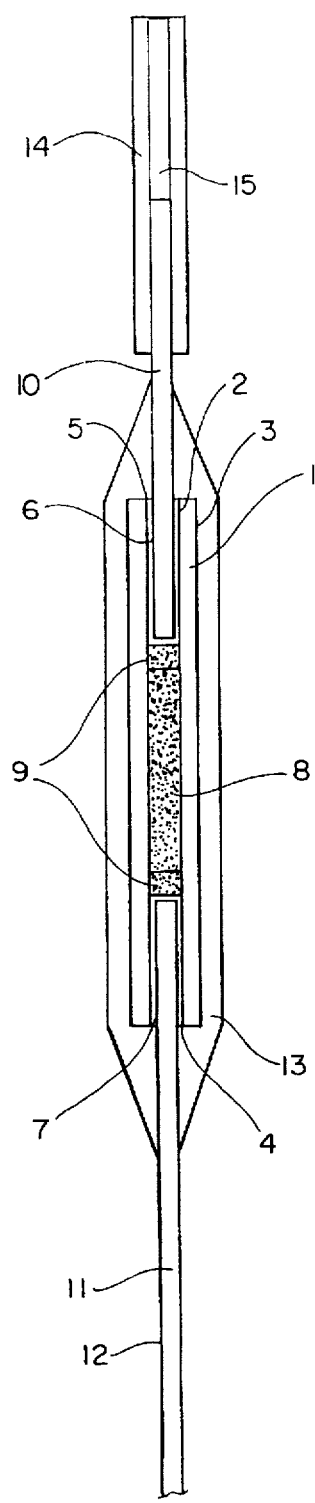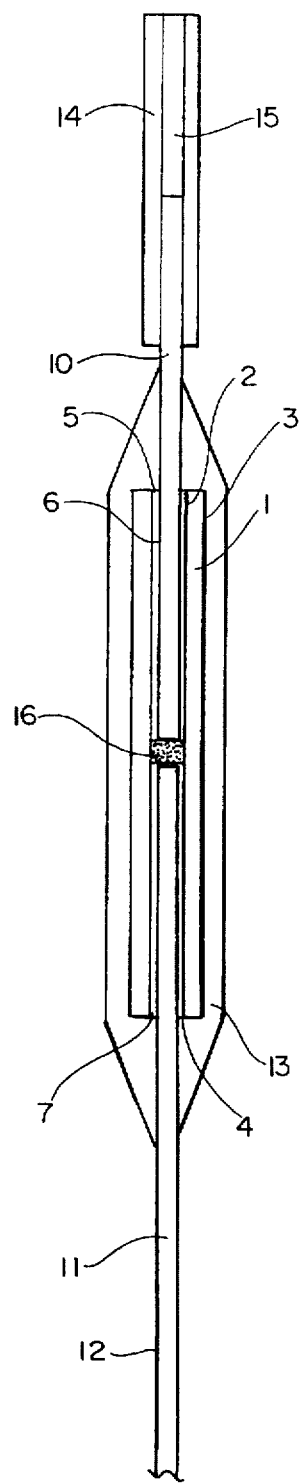

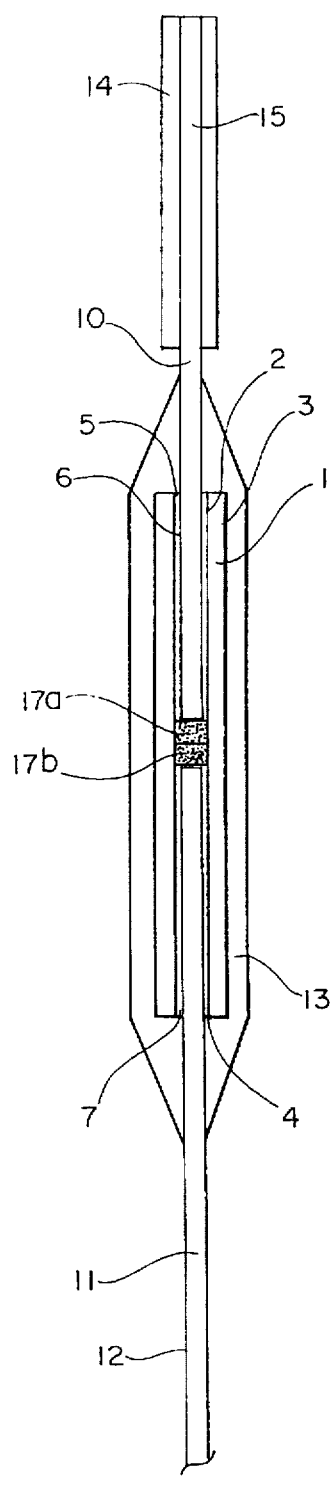
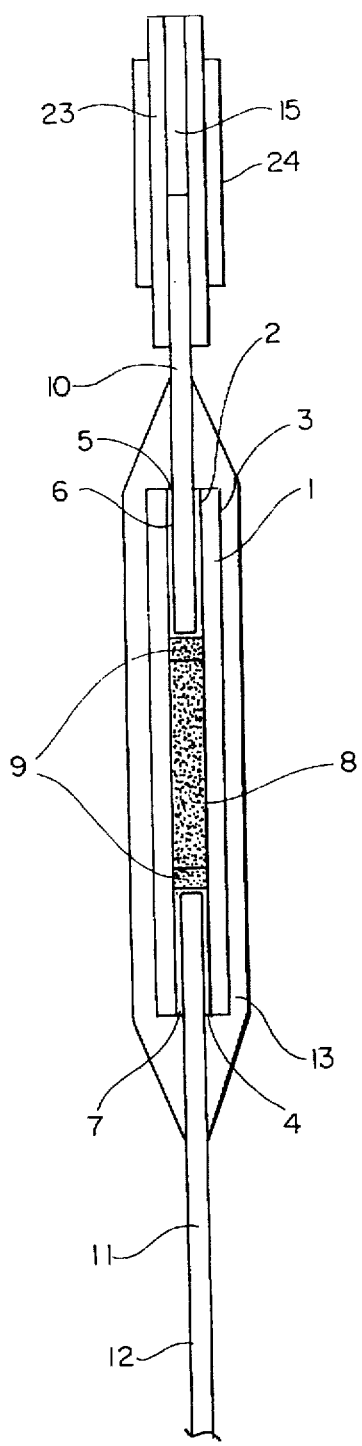

ns. There exists,
therefore, a clear need in the field of capillary electrophoresis for a way to effectively concentrate or otherwise process the components of interest in a dilute sample prior to electrophoretic separation without adversely affecting the electroosmotic flow during capillary electrophoresis, and in a way that minimizes sample loss due to handling.
PRESEPARATION PROCESSOR FOR USE IN CAPILLARY ELECTROPHORESIS

BACKGROUND OF THE INVENTION

Capillary electrophoresis (CE) is an analytical technique useful for efficiently separating small quantities of different molecular species, known as analytes, present in a chemical or biological sample. A sample containing one or more molecular species is introduced into a separation capillary filled with a suitable electrically conductive buffer. Separation is initiated by placing a large electric potential across the ends of the separation capillary. The resultant electrical field induces species with similar physical and chemical properties to migrate down the separation capillary at similar rates and accumulate into bands, also known as zones. These accumulation bands, also referred to as zones, propagate down the separation capillary and are typically observed by monitoring optical absorption or by using other convenient means of detection.

Capillary electrophoresis can be used to separate analytes in samples that have been subjected to various processing procedures, such as concentration, derivatization, cleavage, oxidation, reduction, or the like. Typically these processing steps are performed before injecting the sample into the capillary electrophoresis system. However, these processing steps often result in sample dilution and necessitate the use of additional containers which can contribute to sample loss. It would be advantageous to conduct these operations "on-line" within a capillary electrophoresis system and in close physical proximity to the separation capillary to minimize sample handling, transfer, and dilution.

Dilute samples are often of particular interest in clinical, medical, and biological research settings. Often, however, dilute samples cannot be analyzed effectively because the concentration of analyte within the band of accumulation is below that which is detectable. Thus, sample concentration prior to or during electrophoretic separation is required. In addition to suffering from the sample handling problems described above, "off-line" methods for sample concentration prior to capillary electrophoresis are exceedingly time-consuming. Thus, in order to enhance the performance of CE, various on-line analyte electrokinetic focusing techniques have been developed. Electrokinetic techniques generally are those that utilize the induced motion of charged substances subjected to an electrical field. Electrokinetic focusing techniques currently in use include pH dependent sample focusing, isotachophoresis (ITP), and field amplification. However, these techniques can only be applied to charged analytes, and furthermore are of limited use in the analysis of dilute solutions. Bands cannot be compressed without limit, and in very dilute solutions, analytes cannot be detected even when employing these more sophisticated focusing techniques.

As an alternative to focusing and other electrokinetic methods for sample concentration, techniques utilizing on-line adsorbing "pre-columns" have been recently introduced. These techniques utilize a substance at the input end of the separation capillary to capture and accumulate the analyte of interest from a dilute sample. After a sufficient quantity of the analyte has accumulated, the analyte is redissolved in a smaller volume of an appropriate solvent and eluted. Capillary electrophoresis may now be initiated on a concentrated sample, improving the delivery of detectable concentrations of the analytes. These on-line sample concentration techniques may also be used to "clean up" or decontaminate samples prior to electrophoresis. For example, some fluids, such as urine, contain relatively large amounts of salts or other contaminants that need to be washed away prior to detecting an analyte that is present in much lower concentrations. However, peak resolution of the eluted, concentrated analyte deteriorates as the quantity of accumulated analyte increases. Peak broadening is a major drawback of known pre-column concentration methods.

Where pre-columns are used, separation effectiveness of the capillary electrophoresis system is also lost because the coatings and solid phase packing materials used to concentrate the sample on-line prior to separation strongly perturb the electroosmotic flow in the separation capillary. A similar perturbation in electroosmotic flow results from coatings and packing materials used to process the sample on-line in other ways, such as by derivatization, reduction, or cleavage. The electroosmotic flow (EOF) is the force applied to the analytes as a consequence of the surface charge in the separation capillary induced by the electric field. A reversal in EOF can reduce the efficacy of the separation by reducing resolution, change analyte migration times, or cause some species to travel in the opposite direction, eventually causing their ejection from the inlet side of the separation capillary.

The numerous problems associated with known off-line and on-line methods of sample concentration and other preseparation processing techniques thus severely compromise CE, rendering it unreliable and irreproducible, and hence unsuitable for analytical applications. There exists, therefore, a clear need in the field of capillary electrophoresis for a way to effectively concentrate or otherwise process the components of interest in a dilute sample prior to electrophoretic separation without adversely affecting the electroosmotic flow during capillary electrophoresis, and in a way that minimizes sample loss due to handling.

SUMMARY OF THE INVENTION

The present invention relates to an apparatus and method of performing preconcentration capillary electrophoresis (PC-CE). In particular, this invention relates to sample concentration, clean-up, and/or processing prior to, or during, capillary electrophoretic separation of analytes that are analyzed across a broad range of disciplines which include, but are not limited to, clinical diagnostics, forensic sciences, environmental chemistry, agrochemical analysis, petrochemical business, food industry, and other branches of analytical science and research. This technology is particularly useful for clinical diagnostics because it permits more rapid and accurate analyses of extremely small quantities of drug metabolites, peptides, and proteins from biological or physiological fluids such as urine, feces, serum, blood, plasma, cerebral spinal fluid, nasal drainage, aqueous humor, various biopsies, tissue homogenates, cultured cells, and/or extracts thereof.

Specifically, the invention provides an on-line preseparation processor for use in capillary electrophoresis having a container with an inner surface, an outer surface, an inlet port, and an outlet port, and a sample processing material disposed therein. The sample processing material, which may be useful for concentrating, decontaminating, or chemically processing components of a sample, is disposed inside the container such that the material is in contact with the inner surface of the container when in use during an electrophoretic separation. Another particularly advantageous feature of the present invention is the use of the sample processing material in the form of a membrane. The use of a membrane is believed to effectively surmount the electroosmotic flow (EOF) reversal problem associated with other CE pre-column concentrators or analyte concentration and processing techniques known in the art.

Also provided by the invention is preseparation processor assembly, which includes a container having therein a sample processing material, preferably in the form of a membrane, means for introducing a sample into the inlet port and for removing a processed sample from the outlet port of the container, via an inlet connection and outlet connection, respectively, and means for sealing the inlet and outlet connections so as to prevent the leakage of liquid from said connections. The preseparation processor assembly can be connected to an existing capillary electrophoresis system by using a connector to attach the sample removal means, typically a microbore capillary electrophoresis tube, to a separation capillary.

The invention also provides a pre-processing capillary electrophoresis system, wherein the outlet port of a container having therein a sample processing material, preferably in the form of a membrane, is connected to the inlet end of a separation capillary. The pre-processing capillary electrophoresis system also includes means for introducing a sample into the inlet port and for removing a processed sample from the outlet port of the container, via an inlet connection and outlet connection, respectively, and means for sealing the inlet and outlet connections so as to prevent the leakage of liquid from said connections.

A method for using the preseparation processor is also provided. The outlet port of a container having therein a sample processing material, preferably in the form of a membrane, is connected to the inlet end of a separation capillary. Means for introducing a sample into the inlet port and for removing a processed sample from the outlet port of the container, via an inlet connection and outlet connection, respectively, and means for sealing the inlet and outlet connections so as to prevent the leakage of liquid from said connections, are also provided, so as to create a preprocessing capillary electrophoresis system. A liquid sample containing at least one analyte is brought into contact with the sample processing material inside the container, and at least one processed analyte is separated by introducing at least one electrically conductive buffer into the preprocessing capillary electrophoresis system and applying an electric field of about 1–60 kV across the preprocessing capillary electrophoresis system. The processed analyte is then focused, preferably using transient isotachophoresis, and its presence is then detected.

Also provided is a method for performing pre-processing capillary electrophoresis that uses an analyte focusing technique to improve resolution of a concentrated analyte that has been eluted from the sample processing material, preferably in the form of a membrane. Transient isotachophoresis is a preferred analyte focusing technique. The pre-processing capillary electrophoresis system is filled with an electrically conductive buffer, and a liquid sample containing at least one analyte is introduced into the inlet port of the container so as to contact and adhere to the sample processing material. Next, a base plug is introduced into the inlet port of the container. At least one concentrated analyte is then eluted from the container by supplying one or more elution buffers that release the analyte from the sample processing material, and immediately thereafter an acid plug is introduced into the inlet port of the container. The concentrated analyte(s) are separated by introducing an electrically conductive buffer into the inlet port of the container and applying an electric field of about 1–60 kV across the preprocessing capillary electrophoresis system, and are then detected using any convenient means of detection.

DESCRIPTION OF THE FIGURES

FIG. 1 shows a magnified view of a preseparation processor assembly, wherein adsorptive particles commonly used in high performance liquid chromatography (HPLC) constitute the sample processing material.

FIG. 2 shows a magnified view of a preseparation processor assembly, wherein the sample processing material is a membrane that is commonly used in analyte extraction.

FIG. 3 shows a magnified view of a preseparation processor assembly, wherein two types of adsorptive materials, typically chemically derivatized membranes, are used as the sample processing material.

FIG. 4 shows a magnified view of the preseparation processor assembly of FIG. 1 with a connector that includes two pieces of organic polymer tubing.

DETAILED DESCRIPTION OF THE INVENTION

Figure 5:
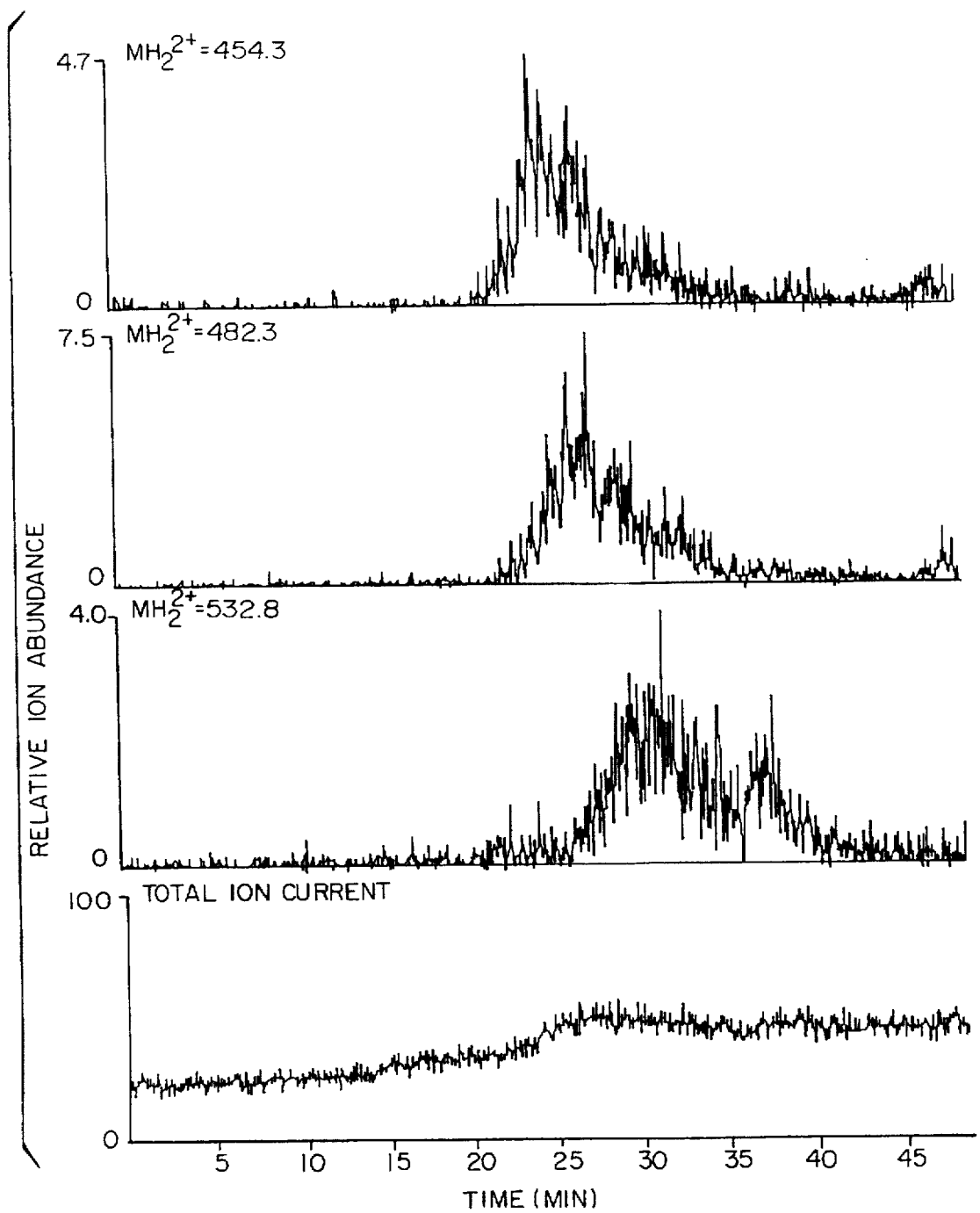
FIG. 5 shows an ion chromatogram of each sample component as well as a total ion current chromatogram for the CE experiment described in Example 3, using a preseparation processor containing adsorptive particulate material.

In capillary electrophoresis (CE), a separation capillary made from a length of microbore capillary electrophoresis tubing (which typically has an internal diameter of about 20–200 μm) is filled with an electrically conductive buffer. A sample of interest, typically containing a multiplicity of molecular species referred to herein as analytes, is then introduced into the separation capillary. The pH and ionic strength of the electrically conductive buffer are generally chosen to maximize the differences in the ionization states of the various molecular species present in the sample. Separation is initiated by placing an electric potential (typically about 1–60 kV) across the ends of the separation capillary.

The applied electric field generates a two component force that acts on the molecular species present in the injected sample. First, an attractive or repulsive electrostatic force, proportional to the mass to charge ratio of the analyte, is applied directly to each ionized species in the sample. This is sometimes referred to as the electrophoretic force. Second, the electrolyte in the buffer experiences a force after the electric field is applied as a consequence of the surface charge in the separation capillary. This second force is called the electroosmotic or endoosmotic flow (EOF), and is directly proportional to the gradient of the applied electric field. The electroosmotic flow occurs because ions located in the double layer present at the capillary/liquid interface move under the force of the applied electric field, and the flow of these ions hydrodynamically drives the flow of the bulk electrolyte within the separation capillary.

The action of the resultant force on the molecular species induces their migration down the narrow diameter capillary tubing. The combined applied force induces species with similar physical and chemical properties to migrate at similar rates and accumulate into bands or zones. The continued application of the electric potential on the ends of the separation capillary causes these bands to propagate down the capillary. An optical detector, is typically employed at, or near, the output end of the separation capillary in order to observe these bands of analytes. The process variables, including, for example, pH, electrolyte species, ionic strength, organic content of run buffer, sample preparation, and loading buffer, temperature, voltage, etc., are commonly adjusted by those skilled in the art in order to achieve effective separation.

Samples are commonly subjected to enzymatic or non-enzymatic chemical processing prior to electrophoresis. For example, radioactive or fluorescence labeling can be performed in order to make additional detection options available. Another example is the facilitation of protein sequencing by subjecting a purified protein sample to an enzymatic digest to generate peptide fragments that can be separated electrophoretically. Such preseparation processing steps, however, contribute to sample loss and dilution.

Dilute samples are difficult to analyze in cases where the concentration of analyte within the band of accumulation is below that which is detectable using standard optical techniques. One way of improving the detection of dilute analytes is to use more sensitive detection methods. For example, the mass spectrometer, a very sensitive and versatile detector, has been employed in conjunction with capillary electrophoresis. The use of a mass spectrometer as a detector is attractive because the detection limits of CE can be extended into a regime of low analyte concentration where optical detection is not effective. Further, mass spectrometry measures charge-to-mass ratio, yielding information about molecular weight, which is more useful for the direct identification of an analyte than optical absorbance. It is therefore possible to detect multiple species present in analyte bands produced by CE. Structural information about the analyte can also be acquired using the fragmentation techniques routinely employed by those skilled in the art of mass spectrometry. Nonetheless, in spite of the improved sensitivity and more complete chemical information provided by mass spectrometric detection, the analysis of extremely dilute samples by capillary electrophoresis remains very challenging.

Many other sensitive and useful detection techniques are known in the art. The technique chosen typically depends on the nature of the analyte. Examples of other useful detection methods are based on optical fluorescence, electrochemical oxidation or reduction, plasma resonance, radioactivity, refractive index, and conductivity. Very dilute analytes can remain undetectable despite the use of the most sensitive of known detection methods.

Another important way to improve detection of dilute analytes, therefore, is to concentrate them prior to, or concurrent with, separation. Preseparation or concurrent analyte concentration, coupled with the use of a sensitive detection method, greatly increases the usefulness and efficacy of CE. Off-line preseparation concentration methods, however, are time-consuming and suffer from various sample-handling risks such as contamination or sample loss due to spill or adsorption onto container walls. Various on-line focusing methods have been developed in response to these problems. Field amplification (also known as sample stacking, analyte stacking, or moving boundary stacking) is one of the simplest methods for on-line sample concentration. The ionic strength differences between the sample matrix and the separation buffer are exploited. The separation capillary is filled with an electrically conductive separation buffer. A sample plug containing a low conductivity buffer is then introduced into the separation capillary, followed by additional separation buffer. Because charged analytes have an enhanced electrophoretic mobility in a lower conductivity environment, when voltage is applied, the electric field is amplified and the analytes quickly accelerate toward an interface at which they are concentrated. In the low conductivity region, the electroosmotic flow is reduced, and analyte movement is generated primarily by electrophoretic mobility at the sample pH. Generation of excess heat in the sample plug is a problem with this technique, and to avoid the heat-induced denaturation of sample components, analytes may be "stacked" at low voltage and then separated at higher voltage.

Field amplification can be increased if a small volume of water is introduced, followed by the sample of interest, and then an acidic stacking buffer. The water acts as a temporary barrier to ion current flow which results in the local amplification of the electric field gradient adjacent to the elution media (R.-L. Chien et al., *J. Chromatog.*, 559, 141–152 (1991); R. J. Nelson et al., *Handbook of Capillary Electrophoresis*, J. P. Landers, ed., CRC Press, Boca Raton, Fla. (1994)). This local change in the electric field gradient provides a barrier against which the analyte zone can become compressed or focused in space by the flow of ionic species from the acidic stacking buffer.

Another class of focusing methods useful for sample concentration is pH-dependent sample focusing, wherein a high pH sample plug is flanked between low pH separation buffer zones. Upon application of voltage, negatively charged analytes in the sample zone migrate toward the anode. Upon entering the lower pH buffer, a pH-induced change in their charge state causes a reversal in the direction of electrophoretic mobility and a reduction in the EOF, resulting in a focusing at the interface between the high pH and low pH zones. Isoelectric focusing is an example of this class.

Isotachophoresis may also be used to focus samples within a separation capillary. Single column ITP-CE (isotachophoresis-capillary electrophoresis) involves the use of a discontinuous buffer system to create isotachophoretic separation conditions prior to the application of an electric potential. The sample is sandwiched between a leading electrolyte and a trailing or terminating electrolyte. Upon application of the potential, the analytes become stacked into discrete zones and progress down the separation capillary. Analyte concentration is uniform within a given zone, and hence analytes are detected as broad plateaus or steps. In transient isotachophoresis, the volume of leading electrolyte and trailing electrolyte used are small, and the discontinuous buffer system disappears because the trailing electrolyte overtakes the leading electrolyte. The buffer thereby becomes continuous, and the stacked zones are separated electrophoretically as they pass through the remainder of the separation capillary, with a small but advantageous amount of dispersion that results in the production of well-resolved peaks, instead of plateaus as in nontransient ITP.

The ITP-CE can be a simple three buffer system, where leading electrolyte is first introduced into the separation capillary, followed by the sample, followed by the trailing electrolyte. The trailing electrolyte is selected such that its mobility is preferably higher at one pH and lower at another pH than the mobility of all charged analytes of interest in the sample. Or the ITP-CE can be a "two buffer" system, wherein a background electrolyte is first introduced into the separation capillary, followed by a plug of leading electrolyte, then the sample of interest, and finally more background electrolyte, which serves as the trailing electrolyte. Alternatively, the background electrolyte can serve as the leading electrolyte, in which case first the background/leading electrolyte is introduced, followed by the sample, then the trailing electrolyte, and finally the background electrolyte. A "one buffer" ITP-CE system is useful where extreme pH is needed to effect a separation. The injected sample is sandwiched between an acid ($H^+$) zone and a base ($OH^-$) zone. When the voltage is applied, the acid and base zones will migrate toward each other, forming a region of low conductivity in the middle. This will lead to moving boundary stacking conditions, which concentrate the analytes. Either the $H^+$ or the $OH^-$ ions can act as the trailing electrolyte.

Preseparation concentration techniques using on-line precolumn concentrators filled with adsorptive material have also been developed. Concentration by adsorption has the additional benefit of facilitating "clean up" of samples contaminated with excessive amounts of salts, detergents, and denaturants. These agents are known to affect the reproducibility of separation by capillary electrophoresis and can interfere with analyte detection, rendering the technique useless for even qualitative analysis of the various molecular species within a sample.

As used herein, the term "on-line" means that the device is disposed within or the technique is conducted within the CE system, in electrical contact with the separation capillary, such that the device or technique is subjected to any electrical potential applied to the separation capillary. Thus, where an on-line precolumn concentrator or other type of preseparation processor is used, the electric potential is not just placed across the two ends of the separation capillary, but rather is applied to the combination of the preseparation processor and the separation capillary, such that it spans both.

Concentration and/or sample processing can be achieved with the various precolumns known in the art, but the effectiveness of the electrophoretic separation is compromised. Considerable peak broadening is commonly observed (See, e.g., A. J. J. Debets et al., *J. Chromatog.*, 608, 151–158 (1992)). Moreover, the coatings and solid phase packing materials employed strongly affect the electroosmotic flow in the separation capillary, producing wide variability in analyte migration times. This particularly troublesome problem is associated with the reversal of EOF produced by preconcentrators known in the art and virtually precludes routine analysis of dilute clinical samples. The strength of this reverse electroosmotic flow appears to vary with the type of packing material used, the nature of the analyte, the bed volume of the packing material, the amount of analyte adsorbed, and the choice of elution solvent (A. J. Tomlinson et al., *J. High Resolution Chromatog.*, 17, 1–5 (1994)), and is not readily amenable to quantification or standardization. Nontransient ITP has been used in conjunction with an on-line pre-column concentrator fabricated from an inert capillary tube, in an effort to focus analytes that have been eluted via electrodesorption; however, the problems produced by the reversal of EOF associated with on-line preconcentrators remain (V. Kasicka et al., *J. Chromatog.*, 273, 117–128 (1983)). The present invention is directed toward solving these problems; it is designed to reduce or eliminate the perturbations in EOF associated with materials used to process samples prior to capillary electrophoretic separation.

Specifically, the present invention provides a preseparation sample processor for use in capillary electrophoresis (CE) comprising a container having therein a sample processing material. Samples appropriate for analysis using the present invention include any liquid sample containing one or more molecular species of interest, referred to herein as a sample component or analyte. The container has an inlet port for introduction of a sample into the container, wherein the sample is brought into contact with the sample processing material, and an outlet port to permit the subsequent removal or elution of analytes or other sample components. During an electrophoretic separation, an electrically conductive buffer is introduced into the container. This buffer comes into physical and, hence, electrical contact with the sample processing material. The sample processing material is preferably in the form of a membrane, which reduces or eliminates problems associated with EOF reversal. Furthermore, when used in conjunction with an analyte focusing technique, as described below in a preferred method for using the preseparation processor, the problem of peak broadening associated with the elution of adsorbed analytes is circumvented.

The container can be fabricated from a material to which analytes do not adhere. It can be made of a metal, metalloid, glass, ceramic, graphite, organic polymer, or a composite of the foregoing materials such as a graphite-spiked polymer. Preferably, teflon is used to fabricate the container.

The utility or effectiveness of the system of the present invention is not limited to any particular shape of container. The container may, for example, be shaped as a cylinder, a sphere, or a box as long as it has an inlet port and an outlet port. Any configuration capable of containing the material used to concentrate or otherwise process the sample is acceptable. Preferably, the container is in the form of a cylindrical tube. The length of the tube is typically between about 1 mm and 10 mm. A wide range of tube bore diameters is useful in the present invention, depending upon the type of material used to process the sample and the type of sample to be analyzed. A microbore tube is preferred, such that the bore diameter is less than about 1000 μm in diameter, more preferably less than about 500 μm in diameter. Particularly convenient is 22 ga stainless steel (Type 304 L) tubing. Commercially available microbore capillary electrophoresis tubing can also be used; the bore diameters of microbore capillary electrophoresis tubing in common use are about 20–200 μm.

When it contains sample processing material, the container of the invention is also referred to herein as a microcolumn. The sample processing material can be used to concentrate, wash, or otherwise process a sample prior to, or during, electrophoretic separation. In a preferred embodiment of the invention, the sample processing material is an adsorptive material that has an affinity for an analyte of interest present in a sample to be analyzed, and is thereby useful for concentrating said analyte prior to electrophoretic separation and/or for removing unwanted materials from the sample such as detergents and salts. Other types of sample processing that can be carried out with the preseparation processor of the invention include analyte cleavage, fluorescence or radioactive labeling or other chemical derivatization, oxidation or reduction, catalysis of a chemical reaction, or the like, and can be enzymatic or nonenzymatic.

The sample processing material used in the microcolumn can include a particulate or fibrous material, a gel, a membrane, a coating, or a combination thereof. The use of one or more membranes, or of particulates, such as a solid phase packing material also known as a resin, commonly used by those skilled in the art of high performance liquid chromatography (HPLC), either alone or in combination, is especially suited to the invention.

Membranes are particularly preferred because of ease of fabrication of the microcolumn, and the minimization of dead volume, which increases resolution. Also, membranes appear to reduce the problems associated with the reversal of EOF. A membrane is typically in the form of a thin, porous, mechanically stable disk. The membrane can itself be made of a material that processes the sample or it can be modified with a variety of materials, such as known chromatographic materials, that effect the processing. In a particularly advantageous form, the membrane is composed of a chemically inert organic polymer matrix, such as PTFE, embedded with adsorbant particles, such as silica. A typical membrane used to practice the invention has a thickness of less than about 1 mm, whereas particulate packing material typically occupies a length of about 0.1 to 10 mm, preferably a length of about 0.1 to 1.0 mm.

The sample processing material preferably includes silica or an organic polymer. In a preferred embodiment of the invention useful for concentrating or decontaminating a sample that contains at least one analyte, the sample processing material is an adsorptive material with an affinity for an analyte. The adsorptive material can be derivatized with a molecule that adsorbs, adheres, or otherwise binds, covalently or noncovalently, an analyte of interest. Derivatization with an aliphatic $C_{18}$, $C_8$, or $C_4$ group is particularly advantageous. In another preferred embodiment of the invention useful for chemically processing the sample prior to or during electrophoretic separation, the sample processing material, preferably in the form of a membrane, is derivatized with a molecular species selected to carry out the desired processing of the analyte. For instance, a proteolytic enzyme such as trypsin, or a disulfide isomerase, such as thioredoxin or protein disulfide isomerase, may be immobilized on a polymer-based particulate or membrane.

Examples of derivatizing agents useful for concentrating or chemically processing analytes include functional groups, ligands, or other molecular species such as a $C_{18}$, $C_8$, $C_4$ or other aliphatic or hydrophobic group; an anionic or cationic group; an antibody or antigen; an amino acid; a peptide; a coenzyme or other biological cofactor, such as biotin; a lectin, glycoprotein, polysaccharide or other carbohydrate-containing moiety; a nucleotide or nucleic acid; a protein or enzyme, such as Protein A, or Protein G; a metal or metal chelate; a molecular superstructure such as $C_{60}$ buckminsterfullerene; or a dye, for example, blue dextran or Cibacron Blue 3GA (Sigma Chemical Company, St. Louis, Mo.). It is to be understood that the preceding list in no way limits the choice of molecules that can be used to derivatize the sample processing material. Likewise, the sample processing material can be underivatized.

Two or more membranes, resins, or other sample processing materials can be placed in series inside the tube, allowing for multiple-step purification, processing and/or separation strategies with minimal dead volume and sample handling. For example, a hydrophobic membrane or resin can be used in conjunction with an anion exchange membrane or an immunoadsorbant membrane, or a $C_{18}$ derivatized membrane can be used in conjunction with a cationic derivatized membrane or a membrane derivatized with a monoclonal antibody.

It may be helpful or necessary to confine, retain or immobilize the sample processing material in the microcolumn. Accordingly, the preseparation processor of the present invention further includes means for confining the sample processing material in the container. Liquids continue to pass through the microcolumn when a means for confining the sample processing material is used. Preferably, one or more frits, plugs, gas or liquid bubbles, physical crimps, constrictions, laser treatments, supports or heat compressions of the container, or any combination thereof, are used. More preferably, a frit or plug is used. Any material sufficiently porous to allow liquid to pass while containing the sample processing material can be used to construct a frit or plug. Silica, polymer, ceramic or metal are preferred fabrication materials. Examples of preferred materials include wool, polyethylene, zirconia, refractory metals, glass, or composite thereof. Silica or polymer wool is particularly preferred. A useful polymer is one that has been fabricated in porous form during curing or processing. Small particles derived from wools or other such materials can be used to form the frit or plug. A frit is typically less than about 1 mm thick. Alternatively, the sample processing material can be immobilized by narrowing, constricting or crimping the internal wall or surface of the tube to confine the sample processing material, as by applying a mechanical force or laser treatment to the container wall or by subjecting it to heat treatment.

Also provided by the invention is a sample processing assembly which adds several useful features to the preseparation processor of the invention. These features include means for introducing a sample into the inlet port of the container, means for removing a processed sample from the outlet port of the container, and means for sealing the inlet and outlet connections so formed to prevent the leakage of liquid. The preseparation processor used in the preseparation processor assembly is as disclosed above.

An example of a convenient means for introducing and removing samples as provided in the preseparation processor assembly is microbore capillary electrophoresis tubing. Typically, a commercially available microbore capillary electrophoresis tube, which typically has an internal diameter of about 20–200 µm, is used. Preferably, the tubing is fabricated from a material such as silica, glass, ceramic, or a chemically inert organic polymer such as polytetrafluoroethylene (PTFE), polyetheretherketone (PEEK), polyimide, or polyethylene. Where the container is in the shape of a cylindrical tube with approximately the same diameter as the microbore capillary electrophoresis tubing, the microbore tubing can be connected to the microcolumn by directly abutting the microbore tubing to the tube. Direct abutment provides a direct route for the flow of fluids from the microbore capillary electrophoresis tubing into the microcolumn, thus minimizing the dead volume in which the sample might pool. Sample pooling compromises recovery and resolution, and is best avoided. The dead volume to be minimized includes the volume accessible to the liquid outside of the tube and the sample introduction means, such as the volume around the outer surface of the sample introduction means but nonetheless inside the sealed inlet connection. Microbore capillary electrophoresis tubing used as a means for introducing and removing samples can be externally coated with a thin layer of organic polymer such as curable epoxy or polyimide for strength. Typically this coating is less than about 50 μm thick.

In the preseparation processor assembly provided by the invention, an inlet connection is formed between the means for introducing the sample into the inlet port of the container and the inlet port itself. Likewise, an outlet connection is formed between the means for removing a processed sample from the outlet port of the container and the outlet port itself. Thus, a means for sealing the inlet and outlet connections so as to prevent leakage of liquid from said connections is included in the preseparation processor assembly. Preferably, the means for sealing the connections is a chemically resistant organic polymer, such as epoxy, polyimide, polyvinyl chloride (PVC), polyethylene, or polypropylene, or glass, ceramic, or a composite of the foregoing materials. More preferably, a chemically resistant organic polymer is used; most preferably, the chemically resistant organic polymer is a curable epoxy. Chemically resistant materials, as the term is used herein, are those that withstand the chemicals commonly used in the art of capillary electrophoresis, such as acetonitrile, methanol, ammonium acetate, dilute acetic acid and other acids; thus any material that shows no detectable degradation during the duration of a capillary electrophoresis experiment, typically about 15 to 40 minutes, is suitable. A material that shows degradation during a typical capillary electrophoresis run and is thus unsuitable for use as a means for sealing the connections in the present invention is uncured polyimide. Some materials, e.g., some commonly available "5 minute" epoxies such as EPOXI-PATCH (Hysol Aerospace, Seabrook NH), may be suitable for single-use applications, but begin to degrade after about 1 to 3 separation experiments. Examples of preferred materials include those that meet USP Plastic Class VI requirements (1995 United States Pharmacopeia, USP 23, National Formulary, NF 18, pp. 1699–1703 United States Pharmacopeial Convention, Inc., 12601 Twinbrook Parkway, Rockville, Md., 20852) such as the bisphenol-novolac epoxy blend, EP42HT (MASTER-BOND, Hackensack, N.J.). The previous examples notwithstanding, it is to be understood that the sealing means is not limited to any particular epoxy or organic polymer, but is to be broadly understood to encompass any means or material that provides an effective liquid seal at the inlet and outlet connections of the preseparation processor assembly, as disclosed above.

The sample processing assembly provided by the invention can further include a means for attaching the sample removal means to a separation capillary. This means for attachment can conveniently take the form of one piece of organic polymer tubing of a length sufficient to allow for the effective sealing of the liquid joint between the preseparation processor assembly and a separation capillary. Preferably, the tubing is inert, i.e., it is chemically nonreactive and is not degraded or otherwise affected by the buffers, reagents or analytes used in capillary electrophoresis. Typically, the connector is about 6–7 mm in length. Preferably, the means for attachment is made up of an outer piece of highly elastic organic polymer tubing, which provides cylindrical pressure directly over the liquid-liquid junction between the output end of the preseparation processor and the input to the capillary electrophoresis tube, surrounding an inner piece of organic polymer tubing sufficient to supply an adequate liquid seal. Preferably, the outer tubing is fabricated from silicone rubber, such as Dow-Corning SILASTIC, and the inner tubing is fabricated from an inert organic polymer such as polytetrafluoroethylene (PTFE), polyetheretherketone (PEEK), or polyethylene.

The present invention further provides a capillary electrophoresis system fitted with a preseparation processor or preseparation processor assembly as disclosed hereinabove, termed herein a "pre-processing capillary electrophoresis system." Preferably, the sample processing material contained in the container of the preseparation processor includes an adsorptive material for concentrating a sample containing at least one analyte. The preseparation processor or preseparation processor assembly is placed in series within a commercially available capillary electrophoresis system, such as the Beckman Instruments P/ACE 2100 capillary electrophoresis system (Fullerton, Calif.), upstream from the separation capillary, such that the outlet port of the container of the preseparation processor is connected to the inlet end of the separation capillary. Typically, the separation capillary is fabricated from silica and has an internal diameter of about 20–200 μm, and a length of about 10–150 cm. Preferably, the microcolumn is adjacent to the separation capillary, and the outlet port of the container of the preseparation processor is within about 15 cm of the inlet end of the separation capillary, more preferably within about 2 cm of said inlet end. To connect the preseparation processor or preseparation processor assembly to the separation capillary, microbore capillary electrophoresis tubing that has been coated or treated on the inside surface using various reagents such as silinizing reagents or hexadimethrine bromide (also known as polybrene) to reduce or eliminate sample adsorption on the capillary walls is preferably used. The capillary electrophoresis system also contains means for introducing a sample into the inlet port of the container, means for removing a processed sample from the outlet port of the container, and means for sealing the inlet and outlet connections formed thereby so as to prevent the leakage of liquid from said connections.

Also provided by the present invention is a method for performing sample processing and subsequent capillary electrophoresis, which method is termed herein "pre-processing capillary electrophoresis." The preseparation processor or preseparation processor assembly of the invention is connected to the inlet end of a separation capillary so as to form a pre-processing capillary electrophoresis system. The pre-processing capillary electrophoresis system preferably includes the preseparation processor or preseparation processor assembly of the invention as disclosed hereinabove, separation capillary, means for detecting analytes during or after separation, means for applying an electric field across the system, and any wiring, valving, or tubing needed to connect the various components to one another and perform capillary electrophoresis. The preseparation processor can be pretreated, flushed, washed or cleaned with an electrically conductive buffer or any other necessary or suitable liquid to prepare it for a separation experiment. A liquid sample containing at least one analyte of interest is introduced into the capillary electrophoresis system and brought into contact with the sample processing material in the container of the preseparation processor. In a preferred embodiment, the sample processing material is an adsorptive material, such that one or more analytes adheres to the adsorptive material and thereby becomes concentrated. The sample is introduced into the inlet port of the container. Hydrostatic or hydrodynamic methods, which work by changing the pressure of the sample relative to the pressure of the liquid in the capillary electrophoresis system, can be used to introduce the sample into the inlet port of the container. Hydrostatic methods of sample introduction include the use of vacuum (suction) or pressure (typically about 0.5–30 p.s.i.). Alternatively, the sample can be electrokinetically introduced into the container by applying an electrical field to induce the movement of charged sample components into the inlet port of the container. After contact with the sample processing material, the processed sample is released from the container through the outlet port.

In cases where the sample processing material contains an adsorptive material with affinity for one or more analytes, analytes are released from the container by supplying elution media capable of releasing an analyte of interest from the adsorptive material. For example, an organic solvent can be used to elute an analyte from a $C_{18}$-derivatized adsorptive material, or a buffer containing a cleavage agent can be used to elute an analyte that has become covalently attached to an adsorptive material. Elution can be effected using hydrostatic methods such as suction (vacuum), pressure (typically about 0.5–30 p.s.i.) or gravity injection. Alternatively, analytes can be eluted using an electrokinetic method such as electrodesorption (V. Kasieka et al., *J. Chromatog.* 273, 117 (1983), incorporated herein by reference).

Processed analytes can be separated using protocols commonly used in the art of capillary electrophoresis. At least one electrically conductive buffer is introduced into the capillary electrophoresis system, and an electric field of typically about 1–60 kV is applied across the preprocessing capillary electrophoresis system. The separated analytes are detected according to methods well-known in the art of capillary electrophoresis. Examples of convenient detection methods include monitoring optical absorption or optical fluorescence, mass spectrometry, electrochemical techniques, conductimetric techniques, monitoring radioactivity, and following changes in refractive index.

Multiple sample elution buffers can be used in the system and the method of the present invention. In a multiple-step purification, processing or separation experiment, several different buffers, differing in composition, pH, salt or organic content, can be used. Moreover, the elution, separation, and detection steps can be repeated as needed for complete analysis of the analytes contained in a given sample.

In a preferred method for sample processing and subsequent capillary electrophoresis, an analyte focusing technique is used in conjunction with the preseparation processor of the invention prior to detection of processed analytes. Preferably, the analyte focusing technique is pH dependent sample focusing, isotachophoresis (ITP), or field amplification.

In a particularly preferred embodiment, the sample processing material is an adsorptive material for concentrating a sample, and transient ITP is used to focus the concentrated analytes. The preprocessing capillary electrophoresis system is first filled with an electrically conductive buffer, after which a liquid sample containing at least one analyte is introduced into the inlet port of the container so as to contact the adsorptive material therein. Elution of adsorbed analytes from the container is preceded by injection of a base ($OH^-$) plug into the inlet port of the container and followed by injection of an acid ($H^+$) plug into the container. The acids and bases employed in transient ITP are preferably volatile, such that they are compatible with analyte detection using mass spectrometry. More preferably, the base is about 0.01% to 0.5% ammonium hydroxide solution, most preferably about 0.1% ammonium hydroxide solution. The acid is more preferably about 0.1% to 5% acetic acid, most preferably about 1% acetic acid. Alternatively, the acid employed in ITP can be a combination of ammonium acetate and acetic acid, such as $NH_4OAC$: 1% AcOH. The volumes of acid and base plugs must be small enough to avoid overheating due to the increased electric field in the plugs. Preferably, the volumes are less than about 1 µl, more preferably, less than about 500 nl, most preferably, less than 200 nl. The term "plug" as used in "acid plug," "base plug," or "sample plug," means a small aliquot of liquid. The eluted analytes are then electrophoretically separated and detected as described above.

A preferred embodiment of the apparatus of the present invention is shown in FIG. 1. A container (1) having an inner surface (2) and an outer surface (3) is constructed from a cylindrical tube of polytetrafluoroethylene (PTFE), for example. The container (1) has an inlet port (4) and an outlet port (5) and surrounds a sample processing material (8) and two retaining frits (9), which confine the motion of the sample processing material (8). In this embodiment, the sample processing material (8) constitutes adsorptive particles commonly used in high performance liquid chromatography (HPLC). The sample processing material (8) is disposed inside the tube (1) such that the processing material is in contact with the inner surface of the container when in use during an electrophoretic separation. The frits (9) are fabricated from a polyethylene wool, for example. A piece of microbore glass tubing (10) of the type that is commonly used in capillary electrophoresis is inserted into the outlet port (5) of the tube (1) so as to provide a means for removing a processed sample from the outlet port (5) of the tube (1). An outlet connection (6) is thereby formed at the juncture of the microbore tubing (10) and the outlet port (5). Likewise, a piece of microbore glass tubing (11) of the type that is commonly used in capillary electrophoresis is inserted into the inlet port (4) of the tube (1) so as to provide a means for introducing a sample into the inlet port (4) of the tube (1). An inlet connection (7) is thereby formed at the juncture of the microbore tubing (11) and the inlet port (4). The microbore tubing (10, 11) is constructed from silica, for example, and is coated with a thin external organic polymer layer (12) such as polyimide for physical strength, for example.

The microbore tubing (10, 11) is placed within the tube (1) in a manner adjacent to and directly abutting the frits (9), which allows the ready flow of liquid through the frits (9) and sample processing material (8). The assembly comprising (1), (3), (2), (8), (9), portions of (10) and (11), (4), (5), (6), and (7), is encased in a chemically resistant, curable epoxy coating (13), which provides physical strength and also serves to seal the liquid joints at the outlet connection (6) and the inlet connection (7). A small connector consisting of a length of organic polymer tubing (14) sufficient to allow for the effective sealing of the liquid joint between the preseparation processor assembly and a length of capillary tubing (15) is attached to the opposite end of the microbore tubing (10). This connector (14) facilitates the connection of the preseparation processor to the desired separation capillary.

FIG. 2 shows another preferred embodiment of the apparatus of the present invention. This embodiment is identical to that shown in FIG. 1, with two exceptions: first, the sample processing material consists of a membrane (16), and second, frits are unnecessary for confining the membrane material, although they may be included if desired. The two pieces of microbore glass tubing (10, 11) are inserted into the outlet port (5) and inlet port (4), respectively, of the tube (1) adjacent to and directly abutting the adsorptive membrane (16), so as to allow the ready flow of liquid through the adsorptive membrane (16).

Another preferred embodiment of the apparatus is shown is FIG. 3. In this embodiment, the tube (1) surrounds a two stage sample processing material (17a, 17b). The sample processing material (17a, 17b) in this embodiment is composed of a pair of membranes derivatized using two different types or families of chemistry that facilitate two step purification strategies. As in the embodiment shown in FIG. 2, frits are unnecessary for confining membrane material, but may be included if desired. The two pieces of microbore glass tubing (10, 11) are inserted into the outlet port (5) and inlet port (4), respectively, of the tube (1) adjacent to and directly abutting the sample processing material (17a, 17b) so as to allow the ready flow of liquid through the complete stack of membranes (17a, 17b).

FIG. 4 shows another preferred embodiment of the apparatus of the invention. This embodiment is identical to that shown in FIG. 1 except that in this embodiment the connector (designated (14) in FIG. 1) is made from an outer piece of organic polymer tubing (24) with a high elasticity, and an inner piece of organic polymer tubing (23) sufficient to supply an adequate liquid seal. The outer elastic polymer based connection tube (24) provides cylindrical pressure directly over the liquid-liquid junction between the output end of the preseparation processor (10) and the input to the capillary electrophoresis tube (15). The inner connection tube (23) consists of a length of inert organic polymer tubing sufficient to allow for the effective sealing of the liquid joint between the preseparation processor and the capillary electrophoresis tubing.

Objects and advantages of this invention will now be illustrated by the following examples. However, the particular materials and amounts thereof recited in these examples, as well as other conditions and details, are to be interpreted to apply broadly in the art of capillary electrophoresis and should not be construed to unduly limit this invention.

EXAMPLE 1.
Comparative Separations of Concentrated and Dilute Peptide Mixtures: Preseparation Processor vs. Standard CE Preseparation concentration capillary electrophoresis (PC-CE) using a preseparation processor (FIG. 1) packed with polymer-based $C_{18}$ beads (Polymer Laboratories, Amherst, Mass.) as described in Example B, below, was used to separate a standard peptide mixture containing varying concentrations of peptide. Analyses were performed on a modified Beckman Instruments P/ACE 2100 capillary electrophoresis system (Fullerton, Calif.) coupled to an IBM compatible Reason Technology 486 personal computer (Rochester, Minn.) using system control and data capture and analysis by SYSTEM GOLD software (Beckman Instruments, Fullerton, Calif.). Peptide elution was monitored at 200 nm.

Acetic acid was obtained from Aldrich Chemical Company (Milwaukee, Wis.). HPLC grade methanol and water were obtained from Baxter/Burdick & Jackson (Muskegon, Mich.). Ammonium acetate and trifluoroacetic acid (TFA) were obtained from Sigma Chemical Company (St. Louis, Mo.). The peptide mixture used in these experiments was the peptide standard mixture obtained from Biorad (Cambridge, Mass.), consisting of bradykinin, angiotensin II, α-melanocyte stimulating hormone, thyrotropin releasing hormone, leuteinizing hormone releasing hormone, bombesin, oxytocin, leucine enkephalin, and methionine enkephalin. The separation runs were conducted in the order described below in Examples A through D.

EXAMPLE A.
Standard CE of Peptide Mixture: Concentrated Sample (50 µg/ml).

Capillary electrophoresis without preconcentration (standard CE) was used to separate a peptide mixture (50 µg/ml) using a 7 second pressure (0.5 p.s.i.) injection. Running conditions: bare (uncoated) silica capillary, 50 µm internal diameter (i.d.) ×67 cm length, 60 cm to detector (total separation length of 67 cm); separation voltage of 21.4 kV (4.5 µAmps) across the capillary which was maintained at 24° C.; separation buffer of 2 mM ammonium acetate in 1% acetic acid (175 mM), pH 2.6. All nine proteins were detected within 15 minutes as very sharp peaks.

EXAMPLE B.
PC/CE of Peptide Mixture Using Preseparation Processor: Dilute Sample (1 µg/ml), With and Without Analyte Stacking.

Preconcentration capillary electrophoresis (PC-CE) was used to separate a dilute peptide mixture (1 µg/ml). The preseparation processor used in the following two separations consisted of a 0.5 mm column fabricated from 22 ga 304 L stainless steel tubing, 1 cm long packed with Polysorb RP, 60–100 µm beads (Polymer Laboratories, Inc., Amherst, Mass.) and fitted with polyethylene wool plugs.

A separation utilizing preconcentration electrophoresis was performed using the following protocol. Running conditions: bare (uncoated) silica capillary, 50 µm i.d.×67 cm length, 60 cm to detector including preseparation processor, placed 1.5 cm from inlet; separation voltage of 21.4 kV (2.2 µAmps) for 60 minutes across the capillary which was maintained at 24° C.; separation buffer of 2 mM ammonium acetate in 1% acetic acid (175 mM), pH 2.6.

Prior to sample loading, a 2 minute rinse was performed with separation buffer. The peptide mixture was introduced into the preseparation processor at high pressure over 30 seconds, then washed 3 minutes with the separation buffer. The sample was eluted from the preseparation processor at high pressure for 12 seconds with 80% methanol, 20% dilute aqueous acetic acid (1%), 0.1% TFA, after which it was subjected to a short (12 second) high pressure push with separation buffer. Following the electrophoretic separation, as described above, the unit was washed for 2 minutes with 100% methanol and re-equilibrated with separation buffer for 5 minutes to prepare for the next run. All proteins were detected (in seven peaks, with co-elution of two components) in about 35 minutes. Peaks showed tailing (adsorption onto capillary wall) suggesting possible peptide denaturation. Recovery was estimated at 88%.

Next, a separation utilizing preconcentration electrophoresis with the preseparation processor plus analyte stacking was performed using the protocol described in the preceding two paragraphs with two modifications. First, base (0.1% ammonium hydroxide) was injected for 6 seconds immediately prior to sample elution from the preseparation processor. Second, the high pressure push with separation buffer following sample elution from the preseparation processor was applied for only 6 seconds, rather than 12 seconds. All nine peptide components resolved; some degradation of sample was evident by a multiplicity of peaks. All peaks were very sharp, with minimal tailing. Recovery was estimated at 88%.

EXAMPLE C.
Standard CE of Peptide Mixture—Dilute Sample (1 µg/ml).

Standard CE was used to separate a peptide mixture (1 µg/ml) using a 7 second pressure (0.5 p.s.i.) injection. Running conditions: bare (uncoated) silica capillary, 50 µm×67 cm length, 60 cm to detector (total separation length of 67 cm); separation voltage of 21.4 kV (4.5 µAmps) across the capillary which was maintained at 24° C.; separation buffer of 2 mM ammonium acetate in 1% acetic acid (175 mM), pH 2.6. Baseline only was produced; peptides were undetectable at this level.

EXAMPLE D.
Standard CE of Peptide Mixture—Concentrated Sample (50 µg/ml).

Standard CE was used to separate a peptide mixture (50 µg/ml) using a 7 second pressure (0.5 p.s.i.) injection. Running conditions: bare (uncoated) silica capillary, 50 µm×67 cm length, 60 cm to detector (total separation length of 67 cm); separation voltage of 21.4 kV (4.5 µAmps) across the capillary which was maintained at 24° C.; separation buffer of 2 mM ammonium acetate in 1% acetic acid (175 mM), pH 2.6. Peaks were smeared, due to protein adsorption to capillary, and deterioration of sample. Recovery was about 60% compared to initial electropherogram. Upon cleaning with NaOEt (0.5 M NaOH-50% ethanol) the peaks sharpened and recoveries increased to 90+%.

EXAMPLE 2.
Improved Separation Resolution with the Preseparation Processor using Transient Isotachophoresis Method. Preseparation concentration capillary electrophoresis using mass spectrometric detection of analytes (PC-CE-MS) was performed on a Beckman Instruments P/ACE 2100 capillary electrophoresis system (Fullerton, Calif.) modified for use with electrospray mass spectrometry that was coupled to an IBM compatible Reason Technology 486 Personal Computer (Rochester, Minn.) using system control and data capture and analysis by System Gold software (Beckman Instruments, Fullerton, Calif.). A sector mass spectrometer of the reverse geometry (i.e., magnetic sector-electric sector configuration) (Finnigan MAT, Bremen, Germany) fitted with an electrospray ionization source (Finnigan MAT, Germany) was used as the analyte detector. A 63 cm long silica separation capillary was prepared by flushing with a 50% sodium ethoxide solution in ethanol for 10 minutes using 20 p.s.i. of pressurized nitrogen gas, followed by a similar 10-minute rinse with methanol. The output end of the CE capillary was introduced directly into the electrospray source in a coaxial manner as described by A. J. Tomlinson e t al, *Am. Lab.*, 26, 29–36 (1994).

A preseparation processor as disclosed in FIG. 1 was constructed using a 22 gauge stainless steel tube containing a packed volume about 0.5 mm long of PLRP-S polymer based reversed phase packing material (Polymer Labs, Amherst, Mass.) having a 20 micron particle size and 300Å pores. This packing material was confined by polyethylene wool frits that were placed within the stainless tube using a fine or narrow gauge wire. The microcolumn was fabricated using standard silica based, polyimide coated, capillary electrophoresis tubing with a 50 micron inside diameter. A '5-minute' epoxy (EPOXI-PATCH) was used for both sealing and electrical insulation. After allowing the epoxy to cure overnight, the sample processor was attached to the separation capillary to form an assembly using a connector consisting of a single piece of polyethylene tubing placed onto the end of the glass connecting tube. The entire assembly was preflushed with a CE separation buffer consisting of a 1% acetic acid solution (Aldrich Chemical Co., Milwaukee, Wis.) in water (Burdick & Jackson/Baxter, Muskegon, Mich.).

In the first trial, a mixture of three peptides having the amino acid sequences SIINFEKL, SIINFEKLT, and SGINFEKL, and having a net concentration of approximately 1 picomole/µl, was introduced into the assembly. These peptides were eluted from the stationary phase of the processor apparatus an elution buffer (250 nl) consisting of 80:20:1 MeOH:H$_2$O:TFA (TFA=trifluoroacetic acid).

In the second trial, transient isotachophoresis was added such that eluted analytes were sandwiched between an acidic and a basic buffer in an attempt to cause zone focusing and the attendant improved resolution. An identical amount of the same peptide mixture was introduced into the same processor apparatus after thorough cleaning and equilibration as described above. Base (200 nl) consisting of 0.1% ammonium hydroxide in water was introduced prior to the elution buffer. Next, the elution buffer consisting of 80:20:1 MeOH:H$_2$O:TFA was used to elute the analytes, after which acid (200 nl) consisting of 1% acetic acid in water was introduced. Separation was initiated by applying about 22 kV across the ends of the assembly. A positive potential of 30 kV was applied to the inlet end of the capillary, and the outlet end of the capillary was installed into the mass spectrometer and held at a potential of about 8 kV, such that the electric field spanned the combination of the preseparation processor and separation capillary.

Figure 6:
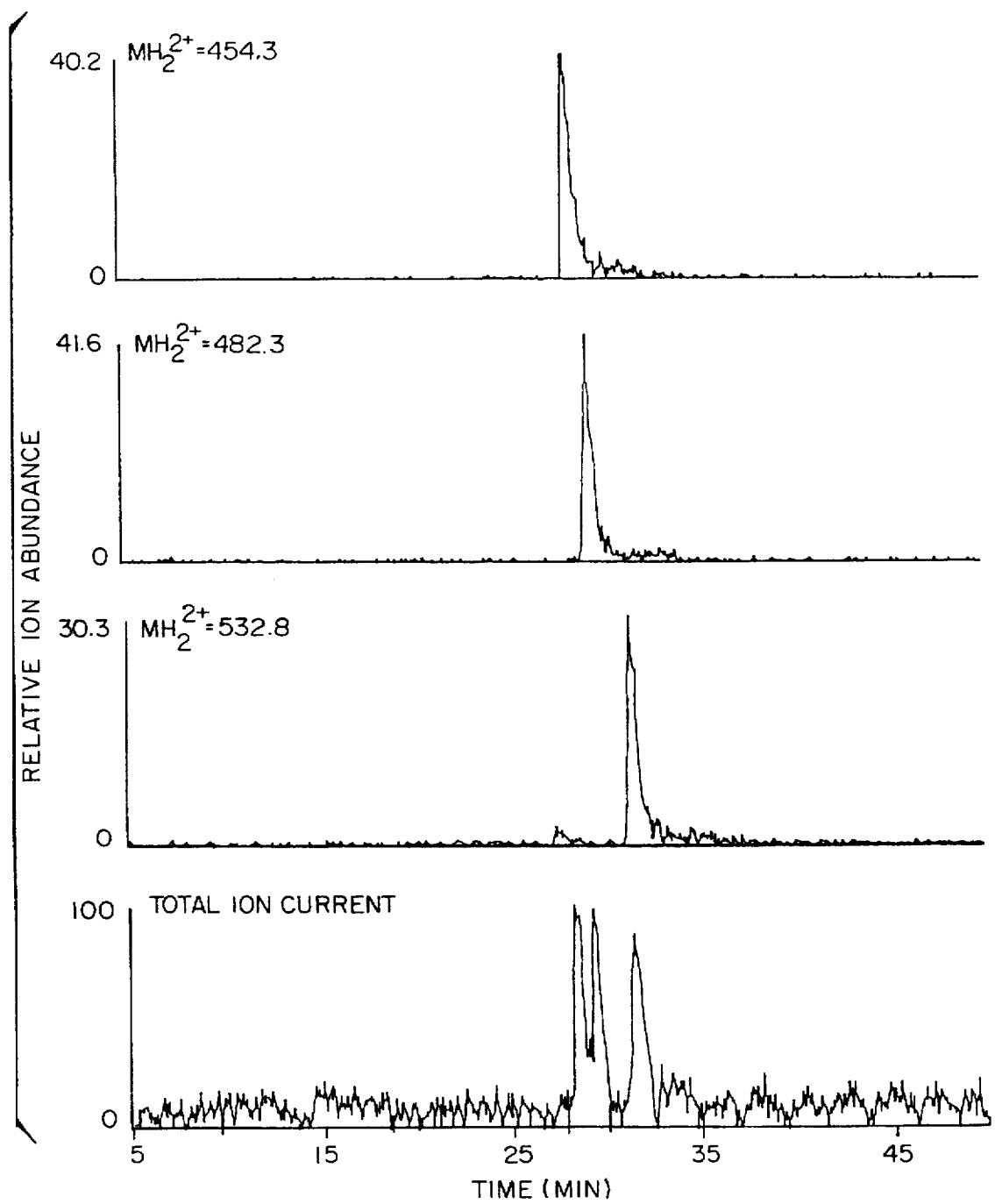
FIG. 6 shows an ion chromatogram of each sample component as well as a total ion current chromatogram for the CE experiment described in Example 3, using a preseparation processor containing adsorptive particulate material, and following the preseparation concentration with transient isotachophoresis to improve analyte resolution.

Results. The results of the first trial, using the simple onestep PC-CE-MS method, are shown in FIG. 5. FIG. 5 shows ion chromatogram of each peptide as well as a total ion current chromatogram. Zone broadening is excessive and compromises both analyte detection and the sensitivity of this assay. This result may be improved substantially by employing the analyte focusing technique of transient isotachophoresis as demonstrated in the second trial. The much improved separation resolution shown in FIG. 6 is obtained.

EXAMPLE 3.
Use of Field Amplification in PC-CE-MS

Method. Capillary electrophoresis with a preseparation processor was used for the separation of three structurally similar peptides. Specifically, capillary electrophoresis was performed on a Beckman Instruments P/ACE 2100 capillary electrophoresis system (Fullerton, Calif.) modified for use with electrospray mass spectrometry that was coupled to an IBM-compatible Reason Technology 486 Personal Computer (Rochester, Minn.) using system control and data capture and analysis by system Gold software (Beckman Instruments, Fullerton, Calif.). A sector mass spectrometer of the reverse geometry (i.e., magnetic sector-electric sector configuration) (Finnigan MAT, Bremen, Germany) fitted with an electrospray ionization source (Finnigan MAT, Germany) was used as the analyte detector. A 63 cm long silica separation capillary was prepared by flushing with a 50% sodium ethoxide solution in ethanol for 10 minutes using 20 p.s.i. of pressurized nitrogen gas, followed by a similar 10-minute rinse with methanol. The output end of the CE capillary was introduced directly into the electrospray source in a coaxial manner as described elsewhere by A. J. Tomlinson et al. (*Am. Lab.*, 26, 29 (1994)).

A preseparation processor as disclosed in FIG. 1 was constructed using a 22 gauge stainless steel tube containing a packed volume about 0.5 mm long of PLRP-S polymer based reversed phase packing material (Polymer Labs, Amherst, Mass.) with a 20 micron particle size and 300 Å pores. This packing material was confined by polyethylene wool frits that were placed within the stainless tube using a fine gauge wire. The column was fabricated using standard silica based, polyimide coated, capillary electrophoresis tubing with a 50 micron inside diameter. A '5-minute' epoxy (EPOXI-PATCH) was used for both sealing and electrical insulation. After allowing the epoxy to cure overnight, the connector which consisted of a single piece of polyethylene tubing was placed onto the end of the glass connecting tube. The entire assembly was preflushed with a CE separation buffer consisting of 2 mM ammonium acetate in 1% acetic acid.

A mixture (1.4 µl) of three peptides possessing the sequences, SIINFEKL, SIINFEKLT, and SGINFEKL, prepared in separation buffer and having a net concentration of approximately 1 picomole/µl, was introduced into the preseparation processor apparatus using 20 p.s.i. of pressurized nitrogen. A small volume (63 nl) of water was introduced prior to analyte elution. Analytes were eluted from the solid phase using 80:20:1 MeOH:$H_2O$:TFA (125 nl), followed by the introduction of an acidic stacking buffer (125 nl) consisting of 1% acetic acid in water. Analyte focusing and subsequent separation were initiated by applying about 22 kV across the ends of the assembly. A positive potential of 30 kV was applied to the inlet end of the capillary, and the outlet end of the capillary was installed into the mass spectrometer and held at a potential of about 8 kV, such that the electric field spanned the combination of the preseparation processor and separation capillary.

Figure 7:
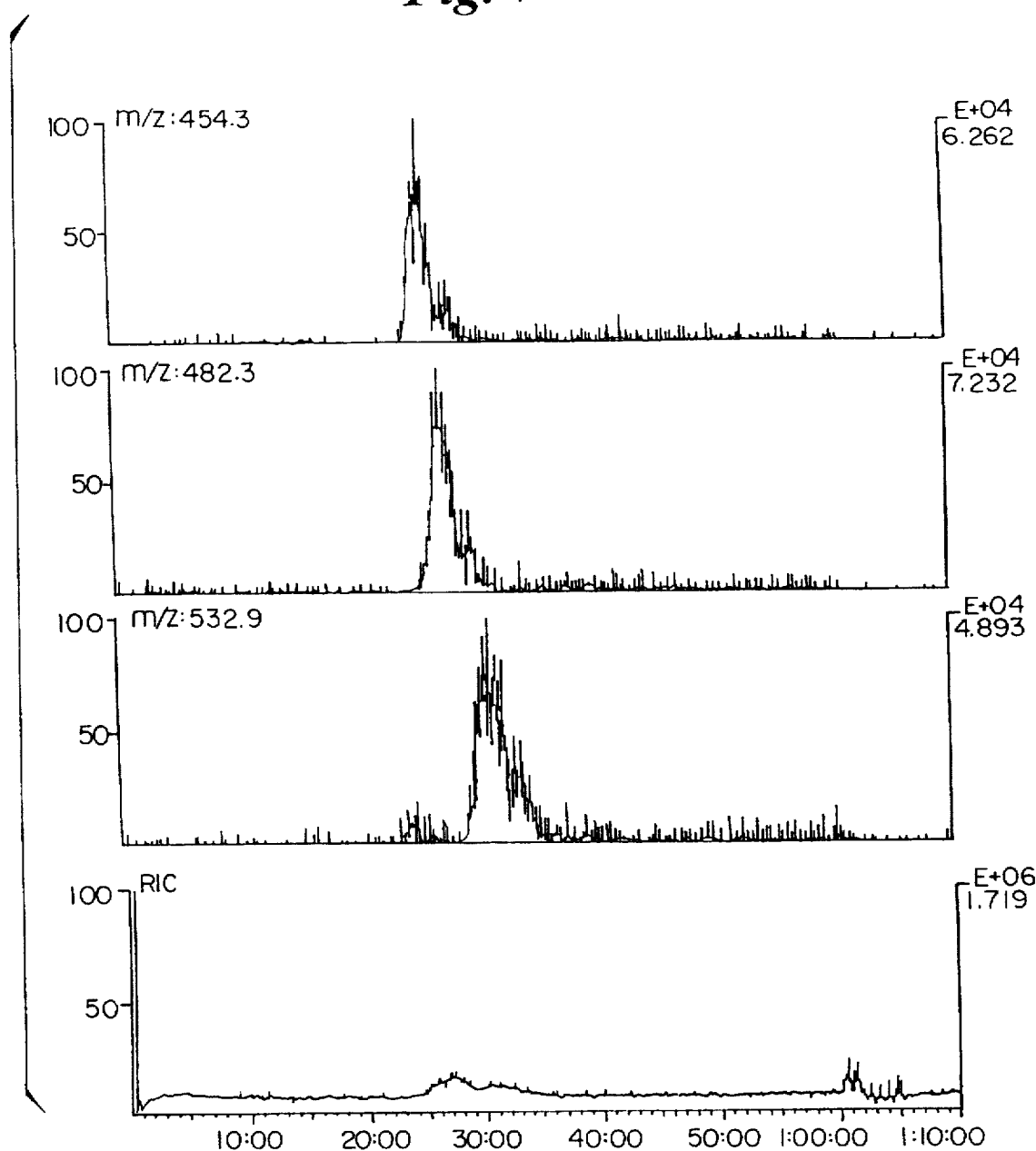
FIG. 7 shows an ion chromatogram of each sample component as well as a total ion current chromatogram for the CE experiment described in Example 4, using a preseparation processor containing adsorptive particulate material, and following the preseparation concentration with field amplification to improve analyte resolution.

Results. Ion chromatograms showing separation of the three peptide analytes utilizing the preseparation processor of the invention combined with field amplification is shown in FIG. 7. Also shown is a total current ion chromatogram. The improvement in resolution attributable to the inclusion of field amplification in separation method is evident from a comparison of the ion chromatograms shown in FIGS. 5 and 7. The resolution of the broad peaks observed in FIG. 7 is improved slightly in FIG. 6, with isotachophoresis. Thus, field amplification techniques may be used to enhance the resolution of a separation when performing PC-CE-MS using the preseparation processor of the invention.

EXAMPLE 4.
Improved Separation Resolution with the Preseparation Processor using Membrane-Based Sample Processing Material and Transient Isotachophoresis A. Method. Capillary electrophoresis with a preseparation processor was used for the separation of a nine component mixture containing bradykinin, angiotensin II, α-melanocyte stimulating hormone, thyrotropin releasing hormone, leuteinizing hormone releasing hormone, leucine enkephalin, bombesin, methionine enkephalin, and oxytocin available from Bio-Rad Laboratories (San Jose, Calif.). Capillary electrophoresis was performed on a Beckman Instruments P/ACE 2100 capillary electrophoresis system (Fullerton, Calif.) modified for use with electrospray mass spectrometry that was coupled to an IBM-compatible Reason Technology 486 Personal Computer (Rochester, Minn.) using system control and data capture and analysis by SYSTEM GOLD software (Beckman Instruments, Fullerton, Calif.). A sector mass spectrometer of the reverse geometry (i.e., magnetic sector-electric sector configuration) (Finnigan MAT, Bremen, Germany) fitted with an electrospray ionization source (Finnigan MAT, Bremen, Germany) was used as the analyte detector. A 63 cm long silica separation capillary was prepared by flushing with a 50% sodium ethoxide solution in ethanol for 10 minutes using 20 p.s.i. of pressurized nitrogen gas, followed by a similar 10-minute rinse with methanol. The output end of the CE capillary was introduced directly into the electrospray source in a coaxial manner as described previously by A. J. Tomlinson et al. (*Am. Lab.*, 26, 29 (1994)). Typically, a sheath liquid consisting of 60:40:1 isopropanol:$H_2O$:acetic acid was employed during electrospray MS.

A preseparation processor as disclosed in FIG. 2 was constructed using a 22 gauge stainless steel tube containing a packed volume about 0.5 mm long of a styrene divinylbenzene based polymer membrane (Varian, San Jose, Calif.). Frits were unnecessary because the membrane is adequately confined by the connecting tubes illustrated in FIG. 2 and discussed in related text. The column was fabricated using standard silica based, polyimide coated, capillary electrophoresis tubing with a 50 micron inside diameter, with a '5-minute' epoxy (EPOXI-PATCH) for both sealing and electrical insulation. Two versions of the microcolumn were fabricated in this work, and each produced identical results. This first consisted of a microcolumn totally encased and sealed in epoxy. In the second, the epoxy was used only to seal the connecting tubes in place, and a combination of this epoxy, air, and the teflon housing of the PAC/E CE unit was used to provide electrical insulation to the processing microcolumn. After allowing the epoxy to cure overnight, a connector consisting of a single piece of polyethylene tubing was placed onto the end of the glass connecting tube. The entire assembly was cleaned by flushing with MeOH and preflushed with a CE separation buffer consisting of a solution containing 2 mM $NH_4OH$: 1% acetic acid solution in water (Burdick & Jackson/Baxter) for approximately 10 minutes.

The peptide mixture (1.4 µl), prepared in separation buffer and having a total protein concentration of approximately 1 picomole/µl, was introduced into the membrane based processor assembly using pressure injection at 20 p.s.i. for 1 minute. Approximately 1.4 picomoles of each peptide was introduced into the apparatus. The analytes were adsorbed onto the solid phase, and were rinsed with run buffer for 3 minutes using standard pressure injection using 20 p.s.i. of pressurized nitrogen gas. As in Example 2, three liquid buffer solutions were used to prepare the system for transient isotachophoresis. First, base (112 nl) consisting of 0.1% $NH_4OH$ in water was introduced into the PC-CE-MS assembly. Next, the peptides were eluted from the membrane-based stationary phase of the processor apparatus using an elution buffer (112 nl) consisting of 80:20:1 MeOH:$H_2O$:TFA. Elution was followed by the injection of acid (56 nl) consisting of 1% acetic acid in water. Separation and isotachophoresis were initiated by applying a potential difference of about 22 kV across the ends of the assembly. A positive potential of 30 kV was applied to the inlet end of the capillary, and the outlet end of the capillary was installed into the mass spectrometer and held at a potential of about 8 kV, such that the electric field spanned the combination of the preseparation processor and separation capillary.

Figure 8:
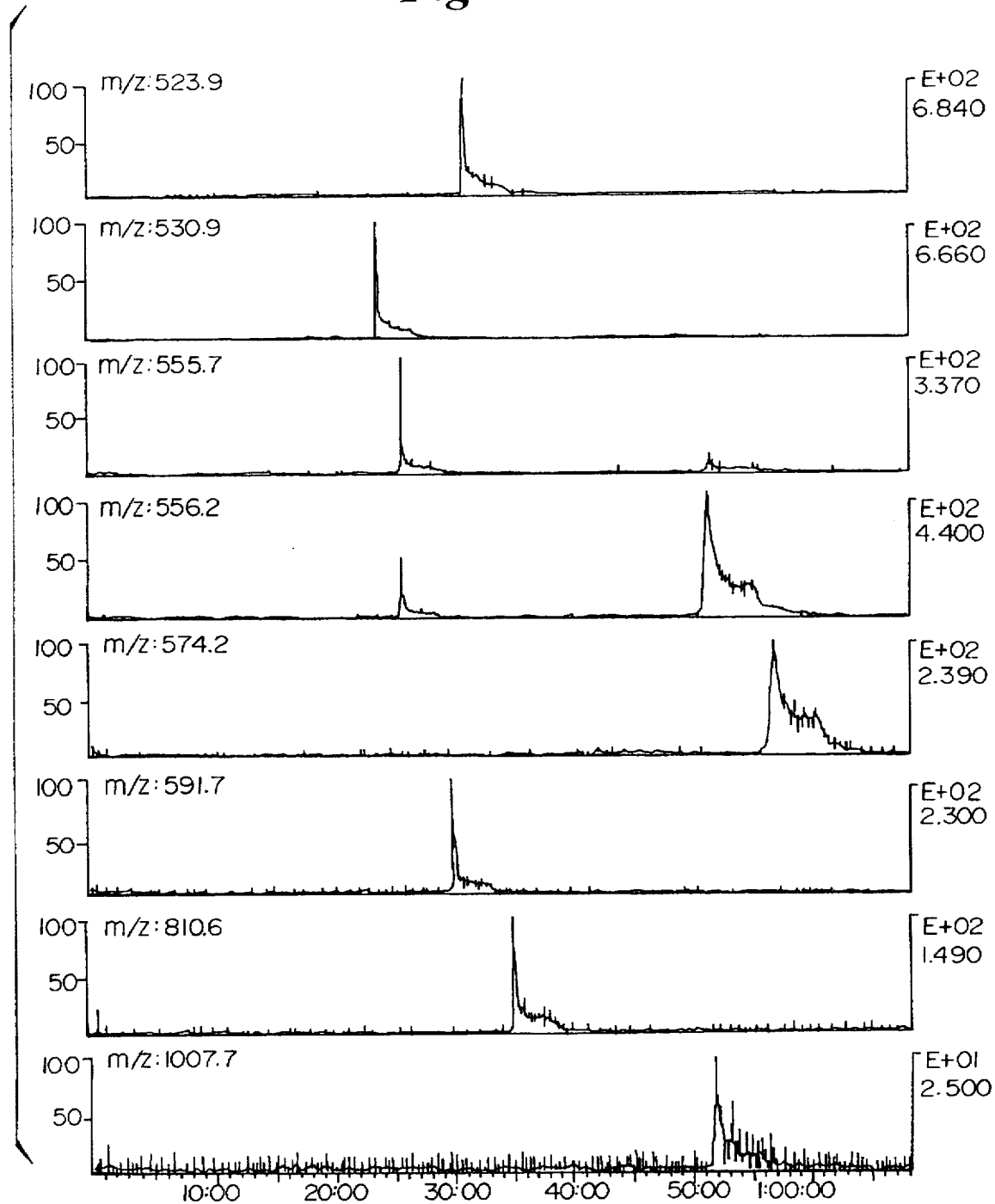
FIG. 8 shows an ion chromatogram of each analyte using a preseparation processor containing an adsorptive membrane, and following the preseparation concentration with transient isotachophoresis to improve analyte resolution.

Results. FIG. 8 shows the ion chromatogram of each analyte using transient isotachophoresis with a membrane-based PC-CEMS microcolumn. The advantages of using membrane-based versus particulate-based solid phase packing materials in the preseparation processor can be seen by comparing the data in FIGS. 5, 6, and 8. Use of a membrane results in a dead volume that is much smaller compared to that produced using the more familiar solid phase materials. This reduction in dead volume allows a reduction in the volume of the elution buffer used. These conditions lead to a marked improvement in the resolution observed in the separation. Thus, analyte focusing via transient isotachophoresis may be used successfully with a preseparation processor assembly that contains a membrane-based solid phase processing material.

EXAMPLE 5.
Larger Volumes of Leading and Trailing Buffers Improve Separation Resolution with the Preseparation Processor using Membrane-Based Sample Processing Material and Transient Isotachophoresis Method. Capillary electrophoresis with a preseparation processor was used to separate a nine-component peptide mixture containing bradykinin, angiotensin II, α-melanocyte stimulating hormone, thyrotropin releasing hormone, leuteinizing hormone, releasing hormone, leucine enkephalin, bombesin, methionine enkephalin, and oxytocin available from Bio-Rad Laboratories (San Jose, Calif.). Capillary electrophoresis was performed on a Beckman Instruments P/ACE 2100 capillary electrophoresis system (Fullerton, Calif.) modified for use with electrospray mass spectrometry that was coupled to an IBM compatible Reason Technology 486 Personal Computer (Rochester, Minn.) using system control and data capture and analysis by SYSTEM GOLD software (Beckman Instruments, Fullerton, Calif.). A sector mass spectrometer of the reverse geometry (i.e., magnetic sector-electric sector configuration) (Finnigan MAT, Bremen, Germany) fitted with an electrospray ionization source (Finnigan MAT, Germany) was used as the analyte detector. A 63 cm long silica separation capillary was prepared by flushing with a 50% sodium ethoxide solution in ethanol for 10 minutes using 20 p.s.i. of pressurized nitrogen gas, followed by as a similar 10-minute rinse with methanol. The output end of the CE capillary was introduced directly into the electrospray source in a coaxial manner as described previously by A. J. Tomlinson et al. (*Am. Lab.*, 26, 29 (1994)). Typically, a sheath liquid consisting of 60:40:1 isopropanol:$H_2O$:acetic acid was employed during electrospray MS.

A preseparation processor as disclosed in FIG. 2 was constructed using a 22 gauge stainless steel tube containing a packed volume about 0.5 mm long of a styrene divinylbenzene based polymer membrane (Varian, San Jose, Calif.). Frits were unnecessary because the membrane is adequately confined by the connecting tubes illustrated in FIG. 2 and discussed in accompanying text. The microcolumn was fabricated using standard silica based, polyimide coated, capillary electrophoresis tubing with a 50 micron inside diameter, and a '5-minute' epoxy (Epoxi-Patch) for both sealing and electrical insulation. Two versions of the microcolumn were fabricated in this work, and each produced identical results. This first consisted of a microcolumn totally encased and sealed in epoxy. In the second, the epoxy was used only to seal the connecting tubes in place, and a combination of this epoxy, air, and the teflon housing of the PAC/E CE unit were used to provide electrical insulation to the processing microcolumn. After allowing the epoxy to cure overnight, a connector consisting of a single piece of polyethylene tubing was placed onto the end of the glass connecting tube. The entire assembly was cleaned by flushing with MeOH and preflushed with a CE separation buffer consisting of a solution containing 2 mm $NH_4OH$: 1% acetic acid solution in water (Burdick & Jackson/Baxter) for approximately 10 minutes.

The peptide mixture (1.4 µl) prepared in separation buffer and having a total protein concentration of approximately 1 picomole/µl was introduced into the membrane-based processor assembly using pressure injection at 20 p.s.i. for 1 minute. Approximately 1.4 picomoles of each peptide was introduced into the apparatus. Analytes were adsorbed onto the solid phase, and were rinsed with run buffer for 3 minutes using standard pressure injection using 20 p.s.i. of pressurized nitrogen gas. As in Examples 2 and 4, three liquid buffer solutions were used to prepare the system for transient isotachophoresis. First, a base (210 nl) consisting of 0.1% $NH_4OH$ in water was introduced into the PCCE-MS assembly using 20 p.s.i. of pressurized nitrogen for 0.15 minutes. Next, the peptides were eluted from the membrane-based stationary phase of the processor apparatus by injecting a buffer (238 nl) consisting of 80:20:1 MeOH:$H_2O$:TFA using 20 p.s.i. of nitrogen for 0.17 minutes. Then acid (70 nl) consisting of 1% acetic acid in water was injected using 20 p.s.i. of nitrogen for 0.05 minutes. Separation and isotachophoresis were initiated by applying a potential difference of about 22 kV across the ends of the assembly. A positive potential of 30 kV was applied to the inlet end of the capillary, and the outlet end of the capillary was installed into the mass spectrometer and held at a potential of about 8 kV, such that the electric field spanned the combination of the preseparation processor and separation capillary, and by applying 0.5 p.s.i. of nitrogen gas in the forward direction.

Figure 9:
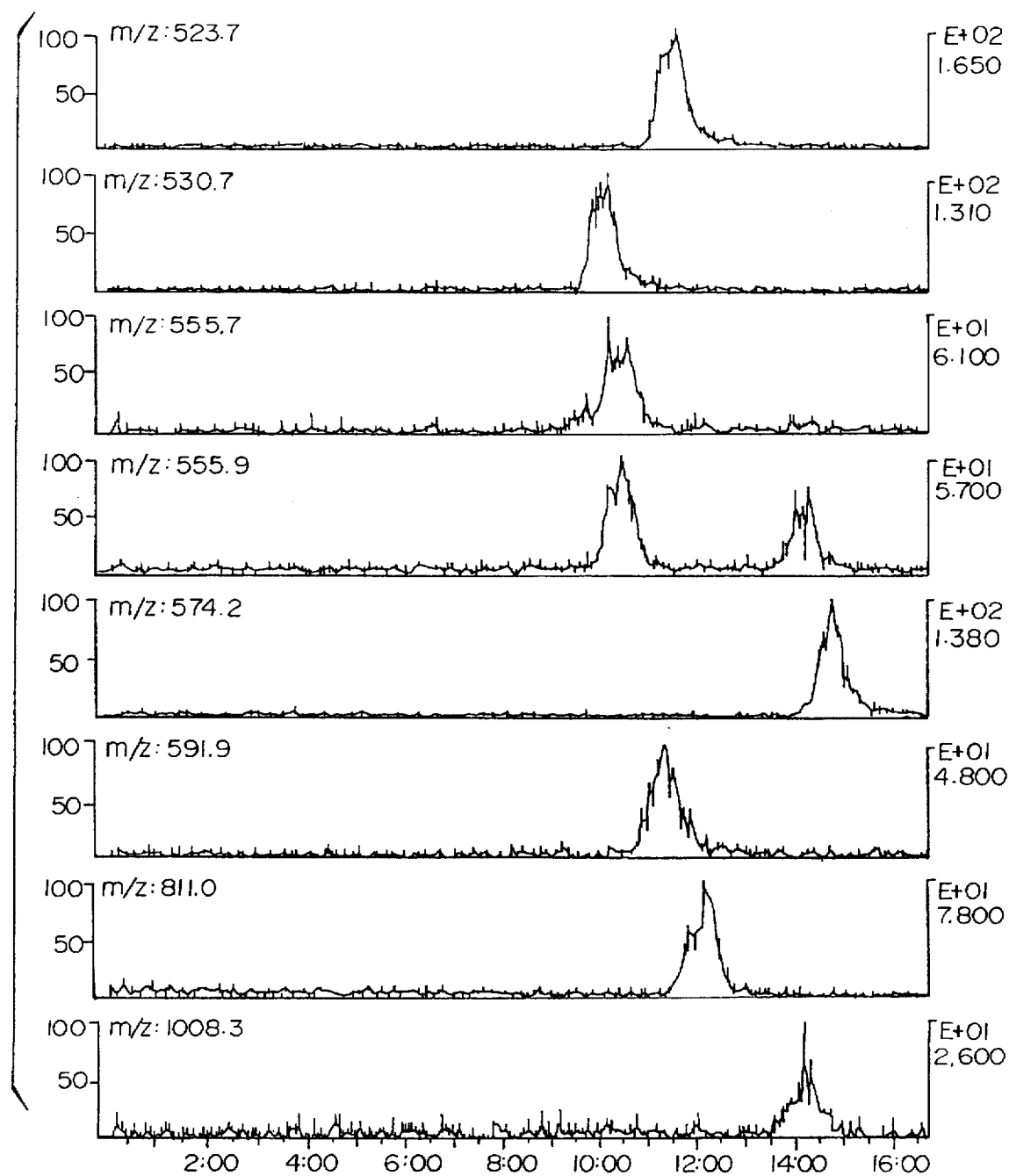
FIG. 9 shows an ion chromatogram of each analyte component of peptide mixture, using a preseparation processor containing an adsorptive membrane, and following the preseparation concentration with transient isotachophoresis using larger volumes of leading, trailing and elution buffers to improve analyte resolution.

Results. FIG. 9 shows the ion chromatogram of each analyte component of peptide mixture containing large amounts of analyte, using a CE separation method utilizing transient isotachophoresis and a membrane-based PC-CE-MS microcolumn. Comparison of the data in FIGS. 8 and 9 shows that enhanced analyte resolution (FIG. 9) can be effected by increasing volumes of leading, trailing and elution buffers. However, this is at the expense of increased analysis times.

EXAMPLE 6.
Processing of Urine Samples Using a Preseparation Processor Containing Membrane-Based Sample Processing Material Method. A capillary electrophoresis system and processor apparatus similar to that used in Example 4 and 5 was used in this experiment to analyze the drug metabolites excreted in patient urine after the administration of the neuroleptic drug Haloperidol. Capillary electrophoresis was performed on a Beckman Instruments P/ACE 2100 capillary electrophoresis system (Fullerton, Calif.) modified for use with electrospray mass spectrometry that was coupled to an IBM compatible Reason Technology 486 Personal Computer (Rochester, MN) using system control and data capture and analysis by System Gold™ software (Beckman Instruments, Fullerton, Calif.). A sector mass spectrometer of the forward geometry (i.e., electric sector-magnetic sector configuration) (Finnigan MAT, Bremen, Germany) fitted with an electrospray ionization source (Analytica, Banford, Conn.) was used for analysis. The metabolites were detected using state-of-the-art PATRIC, position and time resolved ion counting detector (Finnigan MAT, Bremen, Germany). An electrospray voltage of −3.4 kV and an instrument resolution of 1000 were used in this work. The scan range was set to 150–450 Da at 5 seconds per decade, and an 8% mass window was employed during PATRIC™ detection. An 80 cm long silica separation capillary was prepared by flushing with a 50% sodium ethoxide solution in ethanol for 10 minutes using 20 p.s.i. of pressurized nitrogen gas, followed by similar 10 minute rinse with methanol. The output end of the CE capillary was introduced directly into the electrospray source in a coaxial manner as described previously by A. J. Tomlinson et al, *American Lab.* 26, 29–36 (1994). Typically, a sheath liquid consisting of 60:40:1 isopropanol:$H_2O$:acetic acid was employed during electrospray MS.

A preseparation processor as disclosed in FIG. 2 was constructed using a 22 gauge stainless steel tube containing a packed volume about 0.5 mm long of EMPORE (Varian, San Jose, Calif.) membrane containing silica particles derivatized with $C_{18}$ and confined by a proprietary membrane. Frits were unnecessary in this unit because the membrane and solid phase are adequately confined by the connecting tubes illustrated in FIG. 2 and discussed above. The microcolumn was fabricated using standard silica based, polyimide coated, capillary electrophoresis tubing with a 50 micron inside diameter, and a '5-minute' epoxy (EPOXI-PATCH) for both sealing and electrical insulation. Two versions of the microcolumn were fabricated in this work, and each produced identical results. The first consisted of a microcolumn totally encased and sealed in epoxy. In the second, the epoxy was used only to seal the connecting tubes in place, and the necessary electrical insulation was provided by a combination of the epoxy seal, air, and the teflon housing of the PAC/E CE unit. After allowing the epoxy to cure overnight, the sample processor was attached to the separation capillary using a connector consisting of a single piece of polyethylene tubing placed onto the end of the glass connecting tube. The entire assembly was cleaned by flushing with MeOH and preflushed with a CE separation buffer consisting of a solution containing a 50 mM $NH_4OAc$: 10% MeOH:1% acetic acid solution in water (Burdick & Jackson/Baxter) for approximately 10 minutes.

A sufficient volume of urine was collected from a female patient receiving a dosage 0.5 mg of Haloperidol/day. The urine was treated with zinc sulfate and centrifuged to remove the protein. Approximately 10 µl of the supernatant was introduced into the processor apparatus. The analytes were adsorbed onto the solid phase and rinsed with separation buffer for 3 minutes. This rinsing was performed via standard pressure injection using 20 p.s.i. pressurized nitrogen gas in order to remove urea, salts, and other undesirable components from the solid phase. Next, the peptides were eluted from the membrane-based stationary phase of the processor apparatus by injecting a buffer consisting of 100% MeOH using 20 p.s.i. of nitrogen for 0.08 minutes. The peptides were then pushed into the CE separation capillary by a small plug of separation buffer which was injected by applying 20 p.s.i. of nitrogen gas for 0.1 min. Separation and analysis was initiated by applying 20 kV across the ends of the assembly with a positive potential applied to the inlet end of the assembly and a negative potential applied to the outlet end of the assembly, such that the electric field spanned the combination of the preseparation processor and separation capillary.

Figure 10:
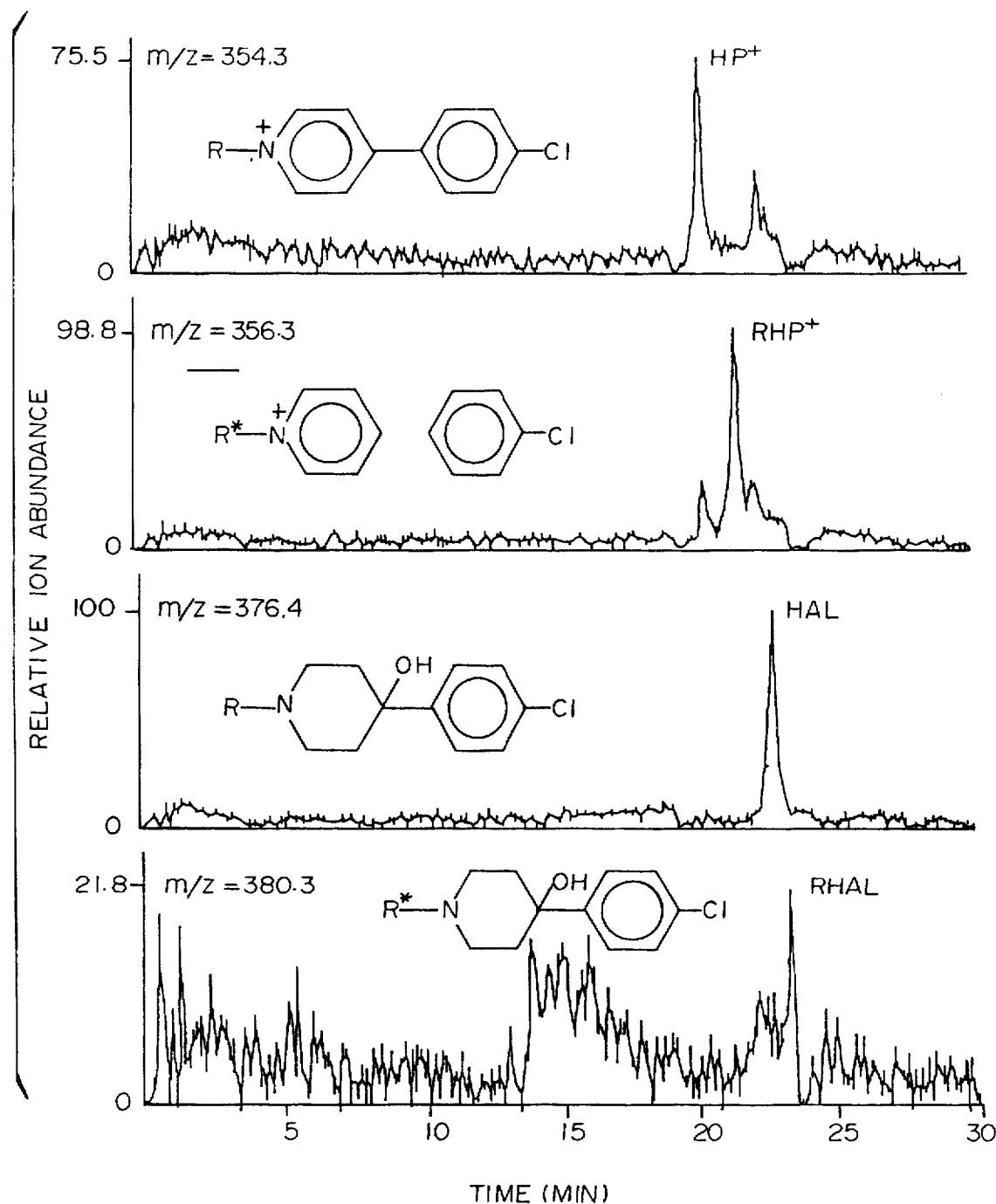
FIG. 10 shows an ion chromatogram of each of the various drug metabolites of halperol found in an unprocessed urine sample, utilizing a preseparation processor containing adsorptive material.

Results. FIG. 10 shows the ion chromatograms of the various drug metabolites. In the absence of the sample processor, the electrospray ionization scanner becomes clogged with urea and ceases to function. Thus, an apparatus and method of analysis are demonstrated which utilize a separation buffer containing a substantial fraction of organic solvent and that successfully remove contaminants from biological samples.

EXAMPLE 7.

Comparison of Conductive and Non-Conductive Preconcentration Cartridges Using a Membrane-based Adsorptive Phase.

Method. All experiments were performed using a Beckman P/ACE 2100 instrument (Fullerton, Calif., USA) coupled to a Reason Technology 486 PC (Rochester, Minn., USA) with system control and data capture by System Gold software (Beckman), as described in previous examples. Dimethylformamide (DMF) detection was by UV at a wavelength of 214 nm.

The preconcentration capillary used in these experiments was prepared from uncoated fused silica tubing (50 µm i.d.), pretreated with potassium methoxide, methanol, and finally CE separation buffer (1% acetic acid in water). The final dimension of the PC-CE capillary was 67 cm×50 µm i.d. A piece of polymeric (SDB) membrane was installed at the mid-point of either a teflon or stainless steel cartridge. A fused silica capillary was set into each end of the cartridge with solvent resistant epoxy resin. Prior to installation, the membrane was activated by washing with MeOH, then CE separation buffer. The entire PC-CE capillary was then conditioned under high pressure (20 psi) for ten minutes with CE separation buffer (1% acetic acid in water). The flow rater through the PC-CE capillary was measured (using a CE separation buffer rinse under high pressure) to ensure that final results could be normalized and compared.

Measurement of EOF in PC-CE capillaries was determined by the migration of dimethylformamide (DMF). This compound is neutral under CE conditions and hence is mobilized by EOF only under CE conditions. A variety of PC-CE cartridge capillaries were made involving a combination of metal, Teflon, one membrane or two membranes, and C-18 solid phase, as summarized in Table 1. The neutral marker dimethylformamide (DMF) was pressure injected via the outlet onto the PC-CE capillary. This ensured that the membrane or solid phase did not come into contact with DMF. The DMF was then pushed into the capillary with CE separation medium (1% acetic acid) under high pressure reverse rinse (0.45 mins, ~800 nL). Migration of DMF was determined under two conditions: 1) low pressure (0.5 psi) infusion; and 2) simultaneous application of 30 kV and low pressure infusion using a CE separation medium of 1% acetic acid in water. Between analyses, the PC-CE cartridge and capillary were rinsed with CE separation medium. These experiments were carried out on virgin membranes or C-18 solid phase and after the adsorptive phase has been contaminated with 1–2 picomoles of a peptide mixture consisting of 5 components OVA, OVAG, OVA9, VSV and $P_2Cl$. Each experiment was conducted in triplicate and all the results are summarized in Table 1. As summarized in Table 1, in all cases, after peptide had passed through the adsorptive phase migration of the DMF marker slowed. Furthermore, whether the membrane/solid phase was encased in either Teflon or metal, the percent slowing was approximately the same. This is summarized in Table 2. With the exception of solid phase in the metal cartridge, all other slowing rates were comparable (~80–90%). In particular the use of 2 membranes in concert (designed to mimic solid phase experiments since adsorptive bed is approximately the same for 2 membranes and 3 mm solid phase), showed no distinguishable difference for metal or teflon as the cartridge. Comparison of the slowing of DMF migration in teflon versus metal (Table 3) is simply a function of flow rate (Table 1 and Table 4) through the adsorptive phase.

EXAMPLE 8.

Use of Analyte stacking in PC-CE-MS.

The capillary electrophoresis system described in Example 3, in conjunction with analyte stacking, was used to separate a mixture of the neuroleptic drug haloperidol (HAL) and six putative metabolites (HAL, CPHP, HNO, HP+, HTP, HTPNO and RHAL.

A preseparation processor as disclosed in FIG. 2 was constructed from uncoated fused silica tubing, pretreated with potassium methoxide, methanol, and finally CE separation buffer. A piece of polymeric (SDB) membrane was installed at the mid-point of a Teflon cartridge. A fused silica capillary was set into each end of the cartridge with solvent-resistant epoxy resin. Prior to installation, the membrane was activated by washing with MeOH, then CE separation buffer. The entire mPC-CE capillary was then conditioned under high pressure (20 psi) for ten minutes with CE separation buffer. All subsequent capillary treatments and sample loading, washing, and elution were also carried out under high pressure (20 psi).

Separation was perform(ed on a Beckman P/ACE 2100 instrument using a purpose built mPC-CE capillary. The sample (~380 attomoles/nL) was loaded in separation buffer by pressure injection for one minute. The membrane was then washed with separation buffer (5 µl) consisting of 50 mM NH$_4$OAc/10% MeOH/1% AcOH and finally the mixture was eluted with 1:1 MeOH: CH$_3$CN (50 nL). Separation buffer consisted of 50 mM NH$_4$OAc, 10% MeOH, and 1% AcOH. Separation was affected at 30 kV (25 gA), with the capillary maintained at room temperature and monitored at 214 nm.

All seven components were baseline resolved and resolution and peak width were comparable to CE analyses and were much improved over PC-CE analysis using solid phase packing material. It is interesting to note that the relatively more hydropholic compound, CPHP, did not adhere as well to the membrane as other compounds and may have been lost during the wash step.

The complete disclosures of all patents, patent documents, and publications, are incorporated herein by reference as if individually incorporated. It will be appreciated by those skilled in the art that various modifications can be made to the above described embodiments of the invention without departing from the essential nature thereof. The invention is intended to encompass all such modifications within the scope of the appended claims.

TABLE 3

Comparison of DMF Migration in Teflon Versus Metal

| No of Membranes | Contamination with Peptide | % Teflon DMF/Metal DMF |
|---|---|---|
| 1 | No | 76.5 |
| 1 | Yes | 85.8 |
| 2 | No | 117.9 |
| 2 | Yes | 116.1 |

TABLE 4

Comparion of Flow Rate in PC-CE

| Comparison | Peptide Contamination | Membrane | Percent |
|---|---|---|---|
| Teflon/Metal | No | 1 | 94.1 |
| Teflon/Metal | No | 2 | 128.6 |

What is claimed is:

1. A preseparation processor for use in capillary electrophoresis comprising a container having an inner surface, an outer surface, an inlet port, an outlet port, and a sample processing membrane disposed inside the container in contact with the inner surface of the container such that a liquid

TABLE 1

Normalized DMF Migration in PC-CE Capillaries

| PC Cartridge | No. of SDB membrane | Flow Rate in PC-CE capillary (µL/min) | Peptide Contamination | Current (µA) | DMF Migration Low Pressure (nL/min) | Average LP only | DMF migration 30 kV + LP (nL/min) | Average 30 kV + LP |
|---|---|---|---|---|---|---|---|---|
| Metal | 1 | 1.7 | No | 6.5 | 49.3, 49.3, 48.7 | 49.1 | 98.6, 101.1, 103.7 | 101.1 |
| Metal | 1 | — | Yes | 6.5 | 47.8, 49.0, 47.6 | 48.1 | 49.6, 77.6, 82.4 | 80.0* |
| Teflon | 1 | 1.6 | No | 6.3 | 46.1, 47.6, 45.3 | 46.3 | 67.7, 81.7, 82.6 | 77.3 |
| Teflon | 1 | — | Yes | 6.3 | 45.9, 46.4, 46.1 | 46.1 | 62.1, 71.6, 72.3 | 68.7 |
| Metal | 2 | 1.4 | No | 6.4 | 49.4, 47.8, 47.8 | 48.3 | 98.0, 113.1, 113.1 | 108.1 |
| Metal | 2 | — | Yes | 6.4 | 46.3, 44.9, 48.2 | 46.5 | 94.8, 98.0, 93.3 | 95.4 |
| Teflon | 2 | 1.8 | No | 6.5 | 56.4, 56.0, 54.4 | 55.6 | 126.0, 128.1, 128.1 | 127.4 |
| Teflon | 2 | — | Yes | 6.5 | 53.6, 52.5, 52.1 | 52.7 | 105.0, 114.5, 112.8 | 110.8 |
| Teflon | 3mm C-18 solid | 1.3 | No | 6.5 | 41.7, 41.4, 40.4 | 41.2 | 97.5, 97.5, 95.8 | 96.9 |
| Teflon | 3mm C-18 solid | — | Yes | 6.5 | 42.3, 41.7, 41.1 | 41.7 | 80.3, 88.1, 91.0 | 86.5 |
| Metal | 3 mm C-18 solid | 2.0 | No | | 59.2, 58.8 | 59.0 | 40.0, —, — | 40.0 |
| Metal | 3mm C-18 solid | — | Yes | | 56.8, 57.7 | 57.2 | 15.0, —, — | 15.0 |

TABLE 2

Percent Slowing of DMF Migration (under LP + 30 kV) After Contamination with Peptide

| PC Cartridge | No. of Membranes | % Slowing of DMF Migration |
|---|---|---|
| Metal Cartridge | 1 | 79.1 |
| Teflon Cartridge | 1 | 88.9 |
| Metal Cartridge | 2 | 88.3 |
| Teflon Cartridge | 2 | 86.9 |
| Teflon | 3 mm Solid Phase C-18 | 89.3 |
| Metal | 3 mm Solid Phase C-18 | 37.5* |

*Based on only a single measurement - since could not obtain any data after 1st run - hence this data point to be regarded with caution.

sample that enters the container through the inlet port and exits the container through the outlet port traverses the sample processing membrane, wherein the sample processing membrane comprises a chemically inert organic polymer matrix embedded with adsorbent particles.

2. A preseparation processor assembly comprising:

(a) a container comprising an inner surface, an outer surface, an inlet port, an outlet port, and a sample processing membrane disposed inside the container in contact with the inner surface of the container such that a liquid sample that enters the container through the inlet port and exits the container through the outlet port traverses the sample processing membrane, wherein the sample processing membrane comprises a chemically inert organic polymer matrix embedded with adsorbent particles;

(b) means for introducing a sample into the inlet port of the container, wherein an inlet connection is formed between the means for introducing the sample and the inlet port of the container;

(c) means for removing a processed sample from the outlet port of the container, wherein an outlet connection is formed between the means for removing the sample and the outlet port of the container; and (d) means for sealing the inlet and outlet connections so as to prevent the leakage of liquid from said connections.

3. A method for performing preprocessing capillary electrophoresis comprising:

(a) providing a container comprising an inner surface, an outer surface, an inlet port, an outlet port, and a sample processing membrane disposed inside the container in contact with the inner surface of the container such that a liquid sample that enters the container through the inlet port and exits the container through the outlet port traverses the sample processing membrane, wherein the outlet port is connected to the inlet end of a separation capillary;

means for introducing a sample into the inlet port of the container, wherein an inlet connection is formed between the means for introducing the sample and the inlet port of the container;

means for removing a processed sample from the outlet port of the container, wherein an outlet connection is formed between the means for removing the sample and the outlet port of the container; and means for sealing the inlet and outlet connections so as to prevent the leakage of liquid from said connections, to create a pre-processing capillary electrophoresis system;

(b) contacting a liquid sample containing at least one analyte with the sample processing membrane inside the container;

(c) separating at least one processed analyte by introducing at least one electrically conductive buffer into the preprocessing capillary electrophoresis system and applying an electric field of about 1–60 kV across the preprocessing capillary electrophoresis system;

(d) focusing the processed analyte using transient isotachophoresis; and (e) detecting the presence of at least one separated analyte.

4. The method of claim 3 wherein the sample processing membrane comprises an adsorptive material for concentrating a sample containing at least one analyte, said method further comprising eluting at least one concentrated analyte from the container by supplying at least one elution buffer that releases an analyte from the adsorptive material, which elution step is performed prior to the separation step (c).

5. The method of claim 3 wherein the sample processing membrane comprises a chemically inert organic polymer matrix embedded with adsorbent particles.

6. A method for performing preprocessing capillary electrophoresis comprising:

(a) providing a container comprising an inner surface, an outer surface, an inlet port, an outlet port, and a sample processing membrane disposed inside the container in contact with the inner surface of the container such that a liquid sample that enters the container through the inlet port and exits the container through the outlet port traverses the sample processing membrane, wherein the outlet port is connected to the inlet end of a separation capillary;

means for introducing a sample into the inlet port of the container, wherein an inlet connection is formed between the means for introducing the sample and the inlet port of the container;

means for removing a processed sample from the outlet port of the container, wherein an outlet connection is formed between the means for removing the sample and the outlet port of the container; and means for sealing the inlet and outlet connections so as to prevent the leakage of liquid from said connections, to create a pre-processing capillary electrophoresis system;

(b) contacting a liquid sample containing at least one analyte with the sample processing membrane inside the container;

(c) separating at least one processed analyte by introducing at least one electrically conductive buffer into the preprocessing capillary electrophoresis system and applying an electric field of about 1–60 kV across the preprocessing capillary electrophoresis system;

(d) focusing the processed analyte; and (e) detecting the presence of at least one separated analyte.

7. The method of claim 6 wherein the sample processing membrane comprises a chemically inert organic polymer matrix embedded with adsorbent particles.

8. A method for performing preprocessing capillary electrophoresis comprising:

(a) providing a container comprising an inner surface, an outer surface, an inlet port, an outlet port, and an adsorptive membrane for concentrating a sample containing at least one analyte, wherein said adsorptive membrane is disposed inside the container in contact with the inner surface of the container such that a liquid sample that enters the container through the inlet port and exits the container through the outlet port traverses the adsorptive membrane, and wherein the outlet port is connected to the inlet end of a separation capillary;

means for introducing a sample into the inlet port of the container, wherein an inlet connection is formed between the means for introducing the sample and the inlet port of the container;

means for removing a processed sample from the outlet port of the container, wherein an outlet connection is formed between the means for removing the sample and the outlet port of the container; and means for sealing the inlet and outlet connections so as to prevent the leakage of liquid from said connections, to create a preprocessing capillary electrophoresis system;

(b) filling the preprocessing capillary electrophoresis system with an electrically conductive buffer;

(c) introducing a liquid sample containing at least one analyte into the inlet port of the container so as to contact the adsorptive membrane inside the container;

(d) introducing a base plug into the inlet port of the container;

(e) eluting at least one concentrated analyte from the container by supplying at least one elution buffer that releases said analyte from the adsorptive membrane;

(f) introducing immediately thereafter an acid plug into the inlet port of the container;

(g) separating at least one concentrated analyte by introducing at least one electrically conductive buffer into the inlet port of the container and applying an electric field of about 1–60 kV across the preprocessing capillary electrophoresis system; and (h) detecting the presence of at least one separated analyte.

9. The method of claim 8 wherein the base and acid are each volatile.

10. The method of claim 9 wherein the base is about 0.01% to 0.5% ammonium hydroxide solution, and the acid is about 0.1% to 5% acetic acid.

11. The method of claim 8 wherein the adsorptive membrane comprises a chemically inert organic polymer matrix embedded with adsorbent particles.

* * * * *

UNITED STATES PATENT AND TRADEMARK OFFICE
CERTIFICATE OF CORRECTION

PATENT NO. : 5,800,692
DATED : September 1, 1998
INVENTOR(S) : Stephen Naylor, Andrew J. Tomlinson, Linda M. Benson, Walter D. Braddock, and Robert P. Oda It is certified that error appears in the above-identified patent and that said Letters Patent is hereby corrected as shown below:

At Col. 20, line 57, "PC-CEMS", should be -- PC-CE-MS --.

At Col. 25, line 3, "perform(ed", should be -- performed --.

Signed and Sealed this

Seventeenth Day of October, 2000

Attest:

Q. TODD DICKINSON

*Attesting Officer*  *Director of Patents and Trademarks*